United States Patent
Ostrow et al.

(10) Patent No.: US 6,443,883 B1
(45) Date of Patent: Sep. 3, 2002

(54) PEMF BIOPHYSICAL STIMULATION FIELD GENERATOR DEVICE AND METHOD

(75) Inventors: Alvin S. Ostrow, Raanana; Joseph Tannenbaum, Jerusalem, both of (IL)

(73) Assignee: Medical Bracing Systems, Ltd., Ráanana (IL)

( * ) Notice: Subject to any disclaimer, the term of this patent is extended or adjusted under 35 U.S.C. 154(b) by 16 days.

(21) Appl. No.: 09/588,287

(22) Filed: Jun. 7, 2000

Related U.S. Application Data

(60) Provisional application No. 60/138,174, filed on Jun. 8, 1999.

(51) Int. Cl.$^7$ ................................................ A61N 1/00
(52) U.S. Cl. ........................................................ 600/14
(58) Field of Search ...................................... 600/9–15

(56) References Cited

U.S. PATENT DOCUMENTS

| | | | | |
|---|---|---|---|---|
| 4,757,804 A | * | 7/1988 | Griffith et al. | 600/15 |
| 5,314,401 A | * | 5/1994 | Tepper | 600/14 |
| 5,743,844 A | * | 4/1998 | Tepper et al. | 600/14 |
| 6,132,362 A | * | 10/2000 | Tepper et al. | 600/14 |

FOREIGN PATENT DOCUMENTS

| WO | WO 00/78267 A1 | * | 12/2000 | | 600/15 |
|---|---|---|---|---|---|

* cited by examiner

*Primary Examiner*—John P. Lacyk
(74) *Attorney, Agent, or Firm*—Edward Langer, Pat.Atty.

(57) ABSTRACT

A multi-functional, modular PEMF biophysical stimulation field generator device and healing system using small coils and a PEMF technique to create a high magnetic flux penetration into hard and soft tissues for treatment of a variety of conditions, including fractures and osteoporosis, to achieve an anticipated shorter healing and rehabilitation time. The orthogonally-arranged coils are sequentially-activated to develop a rotating cylindrical energy field focussed on a target area so as to stimulate bone growth. An activation signal having a combined waveform is used to activate the coils, comprising a high frequency carrier wave, which is amplitude-modulated, by a low frequency treatment wave for optimal penetration of biological tissue. In a preferred embodiment, a pre-form wrap is provided as a cast, brace or splint, containing small magnetizing coils, with the wrap being placed circumferentially around the body part containing the treatment site. By virtue of its modular design, the wrap may contain a portable power source, and it may be opened and the coils removed so that they may be placed over, in or under any orthopedic brace, cast, splint or garment. The coils are arranged to insure maximum focussing of the energy to the treatment site. Minimization of the undesired effects of electromagnetic fields on living tissue is achieved by using the small magnetizing coils, thereby preventing electromagnetic field dispersion to adjacent tissues, by a carrier frequency which improves the electromagnetic field concentration at the treatment site, and by the phasic stimulation which improves the electromagnetic beam concentration in the center, further eliminating electromagnetic field dispersion. The PEMF stimulation also develops an electrical field causing tetanic microcontractions in muscle tissue, thereby offsetting muscle atrophy, a common side effect of immobilization, creating gentle exercise loading, inducing bone growth stimulation. The integrated healing system comprising the inventive device, its placement and activation signal, is engineered to provide optimum therapy by combining the beneficial physiological effects resulting from combined device and treatment modalities to optimize and achieve more efficient results through a combined approach.

41 Claims, 13 Drawing Sheets

Bonestim 2000-2

| Item | Name on Drg. | Type | Pack. Number | Specification | Qty. |
|---|---|---|---|---|---|
| 1 | U1 | MM74HC4060 | MTC16-TSSOP | 14-Stage counter | 1 |
| 2 | U2 | COP8SAC7 | PLCC-V7 | Microcontroller | 1 |
| 3 | U3-U8 | MM74HC4053 | MTC16-TSSOP | CMOS | 6 |
| 4 | U9 | MC78LC50HT1 | | Micropower Voltage Reg. | 1 |
| 5 | U10 | LM358 | | Dual amplifier | 1 |
| 6 | U11 | MC78LC33HT1 | | Micropower Voltage Reg. | 1 |
| 7 | D1-D4 | LM385-1.2 | MA03B-SOT23 | Micropower Voltage Refer. | 4 |
| 8 | T1-T4 | BC307 | | Transistor PNP | 4 |
| 9 | R1 | Resistor | | Resistor 750k-5%,0,125W | 1 |
| 10 | R2 | Resistor | | Resistor 10m-5%,0,125W | 1 |
| 11 | R3-R6 | Resistor | | Resistor 330 Om-5%,0,125W | 4 |
| 12 | R7,R8,R9,R10 | Resistor | | Res. Network 75k, 4 Com. | 1 |
| 13 | R15,R16,R17 | Resistor | | Resistor 100k-5%,0,125 | 3 |
| 14 | R11-R14 | Resistor | | Res. Network 47k, 4 Com. | 1 |
| 15 | R18,R19,R20,R21 | Resistor | | Multi turn trimmer 1k | 4 |
| 16 | R22,R23,R24,R25 | Resistor | | Res. Network 220 Om, 4 Com. | 1 |
| 17 | C1 | Capacitor | | Capacitor 10pF-25% | 1 |
| 18 | C2 | Capacitor | | Capacitor 82pF-25% | 1 |
| 19 | C3-C6 | Capacitor | | Capacitor 6,8 nF-25% | 4 |
| 20 | C7,C8 | Capacitor | | Capacitor 0,1mkF-25% | 2 |
| 21 | S1 | Switch | | 3x1 | 1 |
| 22 | S2 | Button | | | 1 |
| 23 | S4 | Switch | | On-Off | 1 |
| 24 | E1 | Battery-6V | | | 1 |
| 25 | LCD | Display LCD | | RC 0802-A | 1 |
| 26 | X1 | Socket PLCC44 | 151-1546 | Chip Carrier Socket | 1 |
| 27 | | Cabinet | | Plastic case | 1 |

Fig. 6

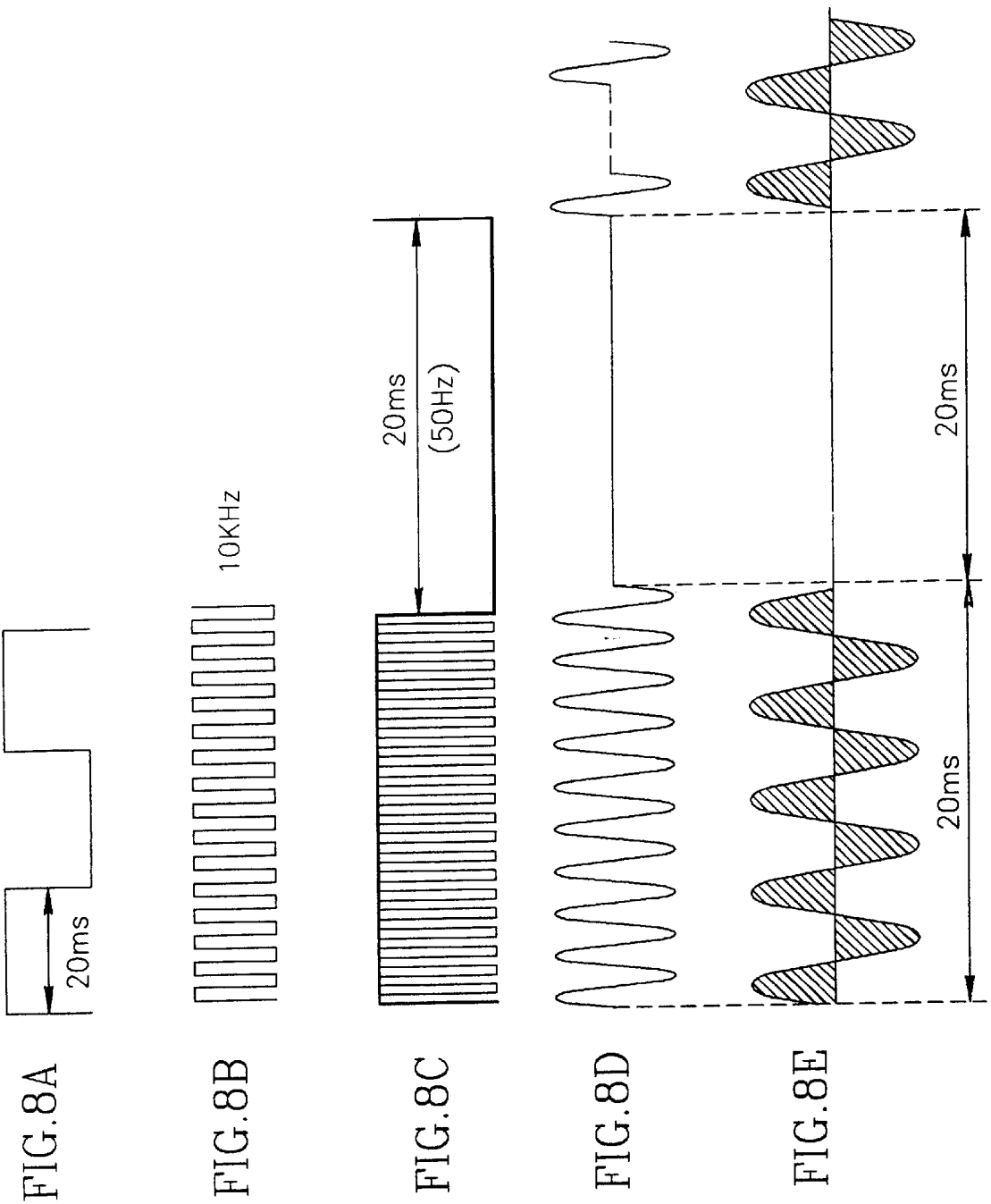

PEMF BIOPHYSICAL STIMULATION FIELD GENERATOR DEVICE AND METHOD

This application claims benefit of Provisional Application Ser. No. 60/138,174 filed Jun. 8, 1999.

FIELD OF THE INVENTION

The present invention relates generally to medical appliances for biomedical therapeutic applications, including osteogenesis, based on application of pulsed electromagnetic fields (PEMF), and more particularly to PEMF's developed in a multi-coil, multi-functional PEMF therapeutic device which optimizes penetration of focussed electromagnetic fields at a treatment site for bone and soft tissue therapy.

BACKGROUND OF THE INVENTION

Electricity is common in living things. In the human body, it provides the basis for thoughts, senses, movement and the rhythm of the heart. As has been learned over approximately the last 50 years, it may also play a crucial role in the functioning of the skeletal system. It is now known that bones carry electric potentials that occur when the bones are at rest. These "bioelectric" potentials are an inherent property of living bone. They are a product of cellular metabolism, thus they disappear when cellular death occurs. It has been shown that active growth plates are electronegative, while the mid-shaft is not. When a fracture occurs, that site also becomes negative and is accompanied by an increase in negativity over the farthest growth plate from the fracture. These intriguing findings lead one to believe that this negative electrical state may be a signal for bone growth.

Bone becomes stronger when subjected to mechanical stress, such as walking, running, weight lifting or hard physical labor. These mechanical stresses are termed weight bearing or bone loading by rehabilitation specialists. When under stress, bone tissue deposits more of the mineral salts that lend strength to bone. When the same stress is removed, bone-resorbing cells (called osteoclasts) go to work and tear down the unnecessary bone. This is why a bone seems to shrink in size when it has been in a cast for some time. This would also partly explain the space osteoporosis that develops in astronauts during long space flights, due to the lack of bone loading in microgravity.

The principles of bone growth and fracture healing follow a process according to Wolff's Law, named after the Orthopedic Surgeon J. Wolff, who discovered this phenomenon in the late nineteenth century. Wolff's Law states that "every change in the form and function of bones or of their function alone is followed by certain definite changes in their configuration in accordance with mathematical laws." This principle states that a bone responds to stress by growing into whatever shape best meets the demands the body makes of it. When a bone is bent, one side is compressed and the other is stretched. When it is bent consistently in one direction, extra bone grows to strengthen the compressed side, and some is absorbed from the stretched side. This law can explain how weight bearing, athletics and the activities of daily living influence the bone structure of a tennis or baseball player, body builder, etc. The Wolff's Law phenomenon of bone reorganization occurs because there is a stimulus to the periosteum to grow new bone at a surface where there is compressional stress, while dissolving bone where there is tensional stress.

An understanding of Wolff's Law wasn't reached until the early 1950s. Research done by I. Yasuda in Japan showed naturally occurring stress generated potentials (SGP's) in bone. This shows that mechanical stress has an effect on the electrical forces in bone. He also found that when a bone is stressed it carries an electropositive charge on the convex (stretched) side, while the concave (compressed) side has an electronegative charge. Bones are made of piezoelectric crystals (calcium apatite) with electrical potential. By mechanically bending a piezoelectric crystal hard enough to deform it slightly, a pulse of current is generated through it. In effect, the pressure "pops" electrons out of their places in the crystal lattice. They migrate down the compression, so the charge on the inside curve of a bent crystal is negative. The potential quickly disappears if the stress is sustained, but when it is released, an equal and opposite positive pulse appears as the electrons rebound before settling back into place.

This finding was a major step in explaining the mechanisms behind Wolff's Law, showing that bone will remodel via deposition of new bone at areas of compression and via resorption of bone at areas of tension. After further examination, it was confirmed that areas of active growth in living bone such as epiphyseal plates and repairing areas, were electronegative when compared with less active areas.

It has also been discovered that when a bone fractures, the entire bone becomes electronegative with a peak electronegativity at the fracture site. This is the same type of direct current that powers a low voltage battery. Since this discovery, the field of electro-biology came into prominence as a science where researchers devote their time to studying the effects of electrotherapy to promote bone growth. Areas of growth in bone have been shown to be electronegative, thereby indicating that osteoblasts are activated by negative charges. By implanting weak electrical current directly into the bone, research has demonstrated that bone formation is increased around the cathode (negative electrode) and decreased around the anode (positive electrode).

Marino and Becker (1970) associated the piezoelectric effect and growth control in bone with a mathematical formula. They demonstrated that on loading, bone will generate a bound surface charge distribution, p(xt) which is nulled by ion current in the permeating interstitial fluid. This process was monitored on a macroscopic level by measuring voltage. A symmetric biphasic pulse is seen, thereby proving the link between mechanical and electromagnetic energy in bone.

To mimic nature's own natural healing mechanisms with electrotherapy, currents of electromagnetism (pulsating electromagnetic fields or PEMEs) are sometimes applied to bones that fail to heal properly. Electromagnetic coils are placed outside the surface of the cast creating weak electromagnetic fields directed to stimulate the fracture site. Like the piezoelectric effect, it is believed that PEMFs stimulate reproduction of bone cells responsible for producing osteogenesis.

In osteology, a callous is defined as bony an cartilaginous material forming a connecting bridge across a bone fracture during repair. Within one to two days after injury, a provisional callous forms, enveloping the fracture site. Bone-forming cells in the periosteum (the bone layer where new bone is produced) proliferate rapidly, forming collars around the ends of the fracture, which grow toward each other to unite the fragments. The definitive callous form slowly as the cartilage becomes ossified. Two to three weeks after injury, strong bony extensions (trabeculae) join the fractured bone ends, and the organized aspect of bone gradually recurs. The callous is resorbed over a period of months.

Bone growth stimulation treatment has seen some success using two main types of biophysical treatment, each of which has been shown to be beneficial in stimulating bone growth. These two types are mechanical signals and electrical signals. These biophysical signals already occur naturally in the human body. However, it is unclear which specific components of the biophysical forces acting on the bone are actually osteogenic and which are just byproducts of bone loading.

The clinical applications of mechanical signals in osteogenesis can be seen as follows. Since past research has found that bone is sensitive to biophysical stimuli induced at low frequencies, the possible role for mechanical stimulation of bone has been further investigated. It is known from past research that a range of frequencies has been shown to persist between 10 and 50 Hz in living bone. Therefore, studies were done by McLeod et al. (McLeod and Rubin, 1992) to see if low amplitude mechanical energy induced at the optimal frequency range could in fact induce an osteogenic response. It was discovered that the osteogenic potential of mechanical stimulation is very similar to electrical stimulation, being very dependent on what frequency is being used. However, the optimal frequency in mechanical signals is higher, with an increasing osteogenic potential up to 60 Hz. This was also found to be dependent on the duration of the signal.

The claims of researchers McLeod and others equating parameters of mechanical stimulation inducing osteogenic potentials in a parallel mathematical relationship to the endogenous electrical stimulation at varying frequencies over time in bone requires further investigation in order to become an exact and dependable science.

There is a clear role for biophysical treatment in the maintenance and treatment of a structurally optimized and secure skeleton, which includes the employment of bone loading and muscular activity. These biophysical stimuli have great potential in the clinical setting if used correctly. They provide a clear and efficacious alternative to pharmaceutical intervention (i.e. biphosphonates, etc), are already occurring in healthy normal bone, are safe at the low levels needed for maximal stimulation and lead to the formation of lamellar bone by going through the entire biological process of bone remodeling. In modern physical medicine terminology, Wolff's law is the underlying basis for a concept known as Specific Adaptation to Imposed Demands (SAID).

These biophysical stimuli as discussed have demonstrated a range of frequencies and mechanical energies (signals) that stimulate osteogenesis. As far as mechanical signals go, at 1 Hz, 100 microstrains produce no response, but when the frequency is raised to 30–60 Hz, an extremely osteogenic response is felt. The case with electrical stimuli is the same. At electrical stimulation below 5 Hz, no osteogenic response is produced, however, once raised to 15 Hz, an extremely osteogenic response is observed. The bone is clearly very sensitive to the frequencies used, so therefore the optimal range of frequencies for stimulating bone must be found.

As new evidence that challenges previous assumptions comes to light, it is necessary to rethink Wolff's Law and the old models and ideas. Historically, it has been thought that the largest effect on bone morphology comes from large biophysical signals. However, new research shows that it is the low magnitude electrical and mechanical signals that are most osteogenic when applied at the appropriate frequency.

It has been shown that bone is very responsive to the amount and rate of deformation or "strain" that it is exposed to. Bone remodeling appears to be directly related to the strain that bone experiences. The question then is, "How is the strain signal actually transformed into a cellular response?" Strain generated potentials (SGP's) are a likely candidate, due to the following facts: 1) they are generated when strain is imposed and 2) potential differences have been associated with growth and repair of bone. It is also known that bone responds to cyclic loading, while a constant load will have little effect on remodeling. The fact that SGPs decay rapidly when deformation ceases supports the correlation between the two. Additionally, studies show that applying an exogenous electricity source to bone can stimulate bone deposition. In general, these studies found that when a DC current is applied, bone is deposited at the negative terminal (cathode), while bone may be resorbed at the positive terminal (anode). More recent research indicates that bone deposition can also be stimulated with alternating electrical fields, which more closely simulate functional activity.

Stimulation of bone growth has multiple applications including treatment of fresh fractures, non-union fractures, and bone disorders such as osteoporosis, and preventative uses, such as preventing bone mass loss in immobilized limbs or in low gravity situations such as outer space.

Specifically, very low frequency (15 Hz) and low intensity stimulation can be very effective at stimulating bone growth (McLeod and Rubin, 1992). It should be noted, however, that SGPs are not the only mechanism being studied as a signal for bone remodeling. One area being pursued concerns the effects on remodeling of shear forces induced by fluid flow through bone. Another area of research involves improvements in nutrient transport to bone cells that may occur during loading. It is possible that many mechanisms may contribute to the adaptations seen in bone with repetitive loading.

The use of electrical and electromagnetic therapy for stimulating growth and repair of living tissue has been known and recognized as an acceptable form of treatment for well over a century. In cases in which there has been a failure to heal, such as non-union fractures, stimulation of repair by electromagnetic fields (EMF) has been shown to upregulate gene expression for matrix proteins and to stimulate matrix synthesis thereby effecting bone repair (EMF Science Review Symposium). Matsunaga et al. (In Vivo May–June; 1996 10(3)) explains that the influence on osteogenesis of magnetic fields (measured in gauss) may be equal to or more important than the influence of electric fields (measured in Hertz). The optimum setting for electromagnetic stimulation was examined by histologically assessing the degree of osteogenesis at different settings of electromagnetic stimulation, and comparing alkaline phosphatase (ALP) activity in the bone marrow. For this experiment, an electromagnetic field generator manufactured by the Institute of Physical and Chemical Research was used. The intensity of the magnetic field was set at eight levels; 0.1, 0.2, 0.4, 1, 2, 4, 6, and 8 gauss (G). The frequencies used were 5, 10, 20, 50, 100 and 200 Hz. Pulse durations were 6, 12, 25, 50 and 100 microsec. Significant ALP elevation and osteogenesis were observed at magnetic field intensities of 0.4, 1 and 2 G. ALP activity did not differ between different frequencies. ALP activity at pulse durations of 25 and 50 microsec was significantly higher than at other pulse durations. The effect of electromagnetic stimulation on osteogenesis greatly depends on the intensity and pulse duration of the stimulation.

Currently, full advantage is not being taken of the use of these biophysical and electrical stimuli in the health care professions, due to lack of knowledge and education in this field. However, as the underlying mechanisms at the molecular and cellular level become understood, it is hoped that these stimuli will be better understood, and as a result, medical instrumentation using this medical technology will therefore become more widely implemented in the clinical and out-patient setting.

There are many prior art patents relating to osteogenesis and electromagnetic therapy of tissues, in animals and humans, using contact electrodes and non-invasively, and a general understanding of the state of the art is facilitated by review of the following patents, which are listed here to give an overview of the level of knowledge:

U.S. Pat. No. 4,266,532 to Ryaby et al./non-invasive induced voltage/tissue repair;

U.S. Pat. No. 4,456,001 to Pecastore/non-invasive/ electromagnetic/bone treatment;

U.S. Pat. No. 4,467,808 to Brighton et al/non-invasive/ osteoporosis treatment;

U.S. Pat. No. 4,674,482 to Waltonen et al/magnetic field/ animal tissue treatment;

U.S. Pat. No. 4,683,873 to Cadossi et al/electromagnetic tissue treatment;

U.S. Pat. No. 5,290,409 to Liboff et al/electromagnetic bone tissue stimulation;

U.S. Pat. No. 5,338,286 to Abbott et al/PEMF field for bone growth stimulation;

U.S. Pat. No. 5,792,209 to Varner/electromagnetic field to decrease osteoporosis;

U.S. Pat. No. 5,825,036 to Ishikawa/EMF to increase recovery power of organs;

U.S. Pat. No. 5,880,661 to Davidson et al/complex EMF generator/bone growth;

U.S. Pat. No. 5,620,463 to Drolet/electrophysiological conditioning for healing;

U.S. Pat. No. 5,743,844 to Tepper et al/PEMF bone growth stimulator;

U.S. Pat. No. 5,891,182 to Fleming/contact electrodes for tissue regeneration;

U.S. Pat. No. 5,919,679 to Blackman et al/magnetic field acting on biological system;

U.S. Pat. No. 5,951,459 to Blackwell/PEMF coil for treating injuries/bone healing;

U.S. Pat. No. 5,997,464 to Blackwell/PEMF coil for treating injuries/bone healing;

U.S. Pat. No. 6,029,090 to Herbst/multi-functional electrical stimulation signals.

As shown in the above list, prior art EMF devices have utilized both invasive implantation (direct stimulation—as disclosed in U.S. Pat. No. RE35,129 to Pethica et al.) and non-invasive magnetic fields. Clearly, a non-invasive procedure is preferable, being painless to the patient and not requiring a hospital stay. Additionally, surgery introduces the possibility of infection. Direct stimulation requires the patient to undergo surgery twice, once upon implantation and once for removal. Although non-invasive devices are therefore usually preferable, prior art non-invasive devices have been limited in their ability to simultaneously become part of or imbedded into an orthopedic brace and treat a fracture site, and have generally achieved this only where a single coil is involved.

Furthermore, the previously known devices did not provide for multiple treatment protocols. In the case of fractures, it is often desirable to begin treatment while a cast is in place and to continue treatment after the cast has been removed. However, this requires two different apparatuses or type of coils, one to be used with the cast and one without the cast.

U.S. Pat. No. 4,616,629 to Moore shows a magnetic coil embedded in an orthopedic cast and U.S. Pat. No. 4,574,809 to Talish et al. describes another form of cast-embeddable coil for electromagnetic therapy. These last two mentioned patents utilize a conventional cast with a removable plug-in connection for a pulse-signal generator. However, these devices are not portable and must be used with a conventional plaster or fiberglass cast.

U.S. Pat. No. 4,066,065 to Kraus recites a jacketing mass that may be provided as a ridged support surface with windings of a coil embedded therein. The Kraus patent has only a single elliptical cylinder-shaped coil.

U.S. Pat. No. 5,344,384 to Ostrow, one of the co-inventors of the present invention, discloses a magnetotherapy apparatus designed as an applicator wrap to be placed around an injured body member to provide a brace, and having magnetic coils for generating an electromagnetic field applied to a target area for tissue therapy.

Japanese Patent published as PCT publication WO85/ 01881 to Onishi, discloses a magnetic field therapeutic appliance arranged as a plurality of housings each having a magnetic field generator joined together and wrapped over a body part, but no multi-functional applications are described, such as a wrap immobilization function.

Prior art devices attempting osteogenesis include the electromagnetic apparatus disclosed in U.S. Pat. No. 5,014, 699 to Pollack et al, where a transducer is placed over a previously formed plaster cast, and is not independently supported. Similarly, the multi-conductor ribbon cable treatment shown in U.S. Pat. No. 4,993,413 to McLeod et al. and the flat bands described in U.S. Pat. No. 4,757,804 to Griffith et al., does not provide an orthotic support. Furthermore, the magnetic fields generated by the aforementioned apparatus are not directionally oriented perpendicularly with respect to a target area. Although the apparatus shown in U.S. Pat. No. 5,100,373 to Liboff et al generates normally directed magnetic fields from two treatment heads, the heads are not positioned for advantageously combining magnetic flux.

Despite the above-mentioned advantages of PEMF treatment, the potential dangers of overexposure to EMF are being explored by government agencies worldwide. Therefore, it would be desirable to provide a device that could best focus the field on the treatment site without exposing large areas of the body to unnecessary EMF's. Medical devices that use PEMFs are regulated for human use by the FDA and other regulatory governing bodies, and are usually regarded as a safe alternative to or as an adjunct to surgical intervention.

PEMFs (pulsed EMF's) represent a relatively complex signal in comparison to simple sinusoidal exposures. PEMF waveforms typically consist of short bursts of narrow pulses in the range of 15–75 Hz. However, waveforms of this type do not penetrate biological tissue efficiently.

Cakirgil et al. in Orthopedics (November 1989 Vol.12/No. 11) compares two-coiled and four-coiled systems for PEMF treatment and concludes that a four-coil system using two perpendicular magnetic fields provides a more effective PEMF treatment. However, the disadvantages of the prior art systems make it an unlikely choice. The existing four coil systems are large and immobile and "require a new design." The four-coil system used by Cakargil cannot be adjusted. Additionally, there is interference between the two perpendicular magnetic fields. The system used by Cakirgil is not within the acceptable FDA boundaries, limits and levels for field strength dosages for safe treatment.

In the technical paper published in NASA technical reports, document ID: 19940027240 N, 94N31746, the role of PEMF fields were investigated as a method of muscle stimulation to alleviate the effects of suspension via unloading muscle and bone.

In the Journal of Orthopedic Sports Physical Therapy (1993), the April 17 issue contains a paper by D. P. Currier et al describing a new method of neuromuscular stimulation using PEMF stimulation for reducing girth loss, pain and muscle weakness.

Thus, it would be desirable to provide a multi-functional osteogenesis device that would provide a portable modular magnetotherapy apparatus which could be removably incorporated within a cast or orthotic brace or preform and that would allow for multiple arrangement and directionality of the electromagnets so as to provide pulsed electromagnetic fields directionally oriented perpendicular to the target area for better focus and penetration at the treatment site.

SUMMARY OF THE INVENTION

Accordingly, it is a primary object of the present invention to provide a. medical appliance for biomedical therapeutic applications, including osteogenesis, based on application of pulsed electromagnetic fields (PEMF), and more particularly to PEMF fields developed in a multi-coil, multi-functional PEMF device which optimizes penetration of focussed electromagnetic fields at a treatment site for bone and soft tissue therapy.

It is another object of the present invention to provide a multi-functional, modular osteogenesis device using small electromagnetic coils that create a high magnetic flux penetration into bone tissue for treatment of fractures and osteoporosis.

It is a further object of the invention to provide sequentially activated coils and a rotating cylindrical energy field focussed at a target area so as to stimulate bone growth. Saturation of the magnetic field is achieved through orthogonal placement of the coils.

It is yet a further object of the invention to provide a waveform composed of a carrier wave and a treatment wave for optimal penetration of biological tissue.

It is a still further object of the invention to provide an osteogenesis device which may be used alone or in combination with a cast, brace or pre-form with adjustable modular coils for use under, over or within a cast, brace, splint or pre-form.

It is yet another object of the invention to provide PEMF neuromuscular stimulation for reducing muscle atrophy as a countermeasure to body unloading effects.

It is yet another further object of the invention to combine PEMF stimulation with a method of splinting, casting or bracing a body part, which is commercially identified by the inventors as the STIM-SPLINT concept.

In accordance with a preferred embodiment of the present invention, there is provided a PEMF biophysical stimulation field generator device comprising:

at least two pairs of electromagnetic coils, individual ones of each pair being arranged at the respective opposite ends of a pair of orthogonal axes;

means for generating a pulsed activation signal applied simultaneously to individual ones of said oppositely arranged coil pair so as to produce oppositely-directed pulsed electromagnetic fields, and subsequently to the other of said oppositely-arranged coil pair, in sequential, alternating fashion, said activation signal having a random frequency component, wherein said activation signal provides PEMF stimulation comprising a relatively high frequency carrier wave amplitude-modulated by a relatively low frequency treatment wave, and wherein said amplitude-modulation introduces a random frequency pattern.

In accordance with a preferred embodiment of the biophysical stimulation signal device of the present invention, a multi-functional therapeutic garment or pre-form wrap is provided containing a plurality of small magnetizing coils, with the pre-form wrap being shaped for placement circumferentially around the body part containing the fracture site. By virtue of its modular design, the pre-form wrap may be opened and the coils removed and placed in, over or under a cast, and the coils may be removably provided in the pre-form wrap containing a portable power source. The electromagnetic coils are aimed at the fracture site in perpendicular relation to the body surface. The perpendicular placement of the coils circumferentially around the treatment site creates a cylinder of treatment and insures maximum focussing of the energy to the treatment site. The electromagnetic coil has a central ferrite core for use with high frequency applications to secure a homogeneous magnetic field. The resulting magnetic fields generated in the device cumulatively interact for deeper magnetic flux penetration to the treatment site.

The coils generate an electromagnetic field (PEMF type) when an activation signal is applied to them, and in accordance with the inventive technique, the activation signal is a combination of a high frequency carrier wave that is amplitude modulated by a low frequency treatment wave. The field generated by the coils is referred to herein as a stimulation field, which reflects the activation signal and carries its waveform directly to the target area, which is the treatment site.

For osteogenesis applications, this multi-coil configuration has been shown to be superior to prior art two-coil systems (per Cakirgil et al., as mentioned in the Background). The coils are designed to apply pulsed, adjustable, low-strength electromagnetic field signals, sufficient to optimally affect specifically targeted fractures, providing enhanced and improved focussed depth penetration to the body tissues to which it is applied. The coils are sequentially activated with coils on the same axis generating oppositely directed electromagnetic fields. Pulsing of the coils is done on alternate axes thereby generating rotational fields.

Unlike the bulky, stationary four coil system of Cakargil, the fast duty cycle of alternating on/off between the dual perpendicular electro-magnets of the present invention does not interfere with the dual planes of PEMF's since they are not used simultaneously. When the dual perpendicular planes of PEMF therapy are applied at fast pulsating rates, a moving energy field in a cylinder of treatment is thus established with a greater saturation gradient of magnetic flux and fields to the treatment site. The electromagnets used in the present invention are smaller than those of the prior art and provide greater, improved therapeutic effects, which will be explained further herein. Further, the electromagnets of the present invention may be adjusted as desired, since they are lightweight and mobile, and do not interfere with the activity of daily living (ADL).

The biophysical stimulation field generator device of the present invention applies an athermal pulsed high frequency homogenous field with combined homogenous AC/DC electromagnetic fields using gauss levels between 2–3 gauss with alternating square wave frequencies varying from 10–30 Hz. The pulsed electromagnetic fields employed in the present invention carry the PEMF stimulation developed by the activation signal to create the least amount of impedance to the body. This configuration, when combined, conveys optimum focussing of the treatment.

In the instant invention, the high frequency carrier wave maintains and increases better depth penetration of the electromagnetic field at the treatment site, allowing the low frequency, which is the actual treatment frequency, to achieve maximum flux depth penetration. The biological tissue is not sensitive to the high frequency carrier wave but reacts to the low frequency wave, thereby naturally filtering the amplitude modulation of the carrier wave with the treatment wave. The energy employed has an athermal effect with duty cycles, by way of example, at 5–30 msec. on and 5–30 msec. off. Optimally, 20 msec is used in the present invention. A 50% duty cycle is applied in the preferred embodiment. The activation signal has an interval frequency of 25 Hz/10 KHz (sinusoidal) with a current level of 5 mAmp. When these parameters and frequencies are combined, a homogenous field is developed at the treatment site.

In the osteogenesis application, three factors in the design of the inventive activation signal, when combined and integrated for the particular application, provide the optimum parameters responsible to induce maximum physiologic and therapeutic effects, and help to minimize the undesired effects of magnetic fields on living tissue: the small magnetizing coils which prevent the dispersion of the electromagnetic field to adjacent tissues; the carrier frequency which is responsible for a marked improvement in the concentration of the magnetic field at the treatment site; and the phasic stimulation which improves the electromagnetic beam concentration in the center, further eliminating electromagnetic field dispersion.

Also in accordance with the principles of the invention, the PEMF stimulation develops an electrical field in muscle tissue. This electrical field developed by the electromagnetic field causes tetanic microcontractions of muscle tissue, and stimulates the neuromuscular junction, thereby offsetting muscle atrophy, a common side effect of immobilization. The microcontractions, which create gentle exercise loading simultaneously induce and/or enhance bone growth stimulation. When a limb is immobilized in a cast or brace or is in a low gravity environment, the unloaded bone is unstimulated due to lack of biophysical and bioelectrical signals. The device of the present invention generates an activation signal that introduces an osteogenic response mimicking the endogenous signals that result from naturally occurring mechanotransduction which stimulates bone growth. One of the signals for induction of mechanotransduction is the gravisensing process of the body. The activation signal generated by the device of the present invention in combination with other features of the device act as an electro-biophysical signal, replacing the normal body stimulus, to promote similar effects accomplished by bone loading.

To mimic the effects of bone loading, the inventive activation signal generates a similar piezoelectric effect on the bone surface to substitute or provide similar signals when the mechanical force is applied. This generated piezoelectric potential may cause molecular binding of bone minerals.

The anticipated shorter healing and rehabilitation time resulting from the application of the present invention, along with the reduced muscle atrophy enables the patient to return to normal activity sooner, while reducing the number of clinic visits required after cast removal.

While not wishing to be bound by theory, it is believed that callous formation and new bone formation of the fractured bone is a result of the inventive activation signal and the electrical potentials created, rather than the direct magnetic field effect (B/H) of the diamagnetic material.

The development of a transverse electric field in a solid material when it carries an electric current and is placed in a magnetic field perpendicular to the current, creates an electrical charge in the tissues that develops bone growth stimulation. This is based on the Hall effect, which is a result of the force that the magnetic field exerts on the moving positive or negative ions that constitute the electric current. Whether the current generated comprises the movement of positive ions, negative ions in the opposite direction, or a mixture of the two, a perpendicular magnetic field displaces the moving electric charges in the same direction sideways at right angles to both the magnetic field and the direction of current flow.

The accumulation of charge on one side of the conductor (i.e. bone) leaves the other side oppositely charged and produces a difference of potential. This phenomenon may be detected by an appropriate meter to read this difference in potential as either a positive or negative voltage, known as the Hall voltage. The sign of this Hall voltage determines whether positive or negative ions are carrying the current. In summary, the magnetic field produces an electric field, and current as per the Maxwell/Lenz laws.

Medical indications that would benefit from using the osteogenesis device of the present invention include osteoporosis, arthritis and others. Additionally, the osteogenesis device can be used for prevention of space osteoporosis.

The combination and integration of all the parameters and properties of the invention as described herein, and other features and advantages of the invention, will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which:

FIG. 3b is a cross-sectional view taken along section line A—A of FIG. 3a;

FIG. 6 shows a list of typical component parts used to implement the device;

FIGS. 8a–e show the activation signal waveform diagrams comprising, respectively, a treatment pulse, carrier pulse, mixed waveform, sinusoidal output waveform, and magnetizing current pattern.

DETAILED DESCRIPTION OF THE PREFERRED EMBODIMENTS

With specific reference now to the figures in detail, it is stressed that the particulars shown are by way of example and for the purpose of illustrative discussion of the preferred embodiments of the present invention only, and are presented in the cause of providing what is believed to be the most useful description principles and conceptual aspects of the invention, based upon the medical literature.

Figure 1:
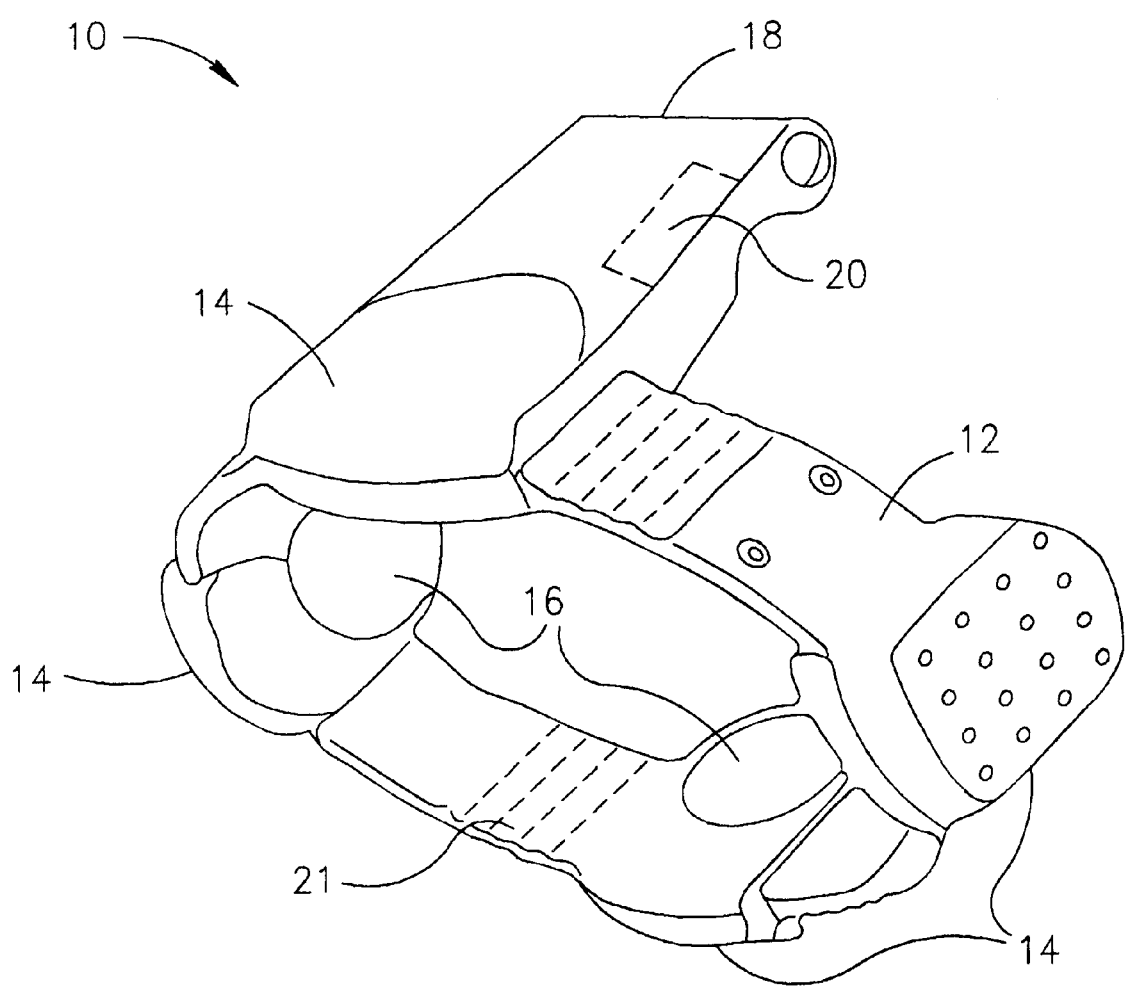
FIG. 1 is a perspective view of a preferred embodiment of a PEMF biophysical stimulation field generator device of the present invention.

Referring now to FIG. 1, there is shown a perspective view of a preferred embodiment of the biophysical stimulation field generator device 10 of the present invention, in an osteogenesis application. Device 10 is provided as a therapeutic pre-form wrap or garment, which in the particular embodiment shown, forms an adjustable strap 12 with four coil housings 14. Electromagnetic coils 16 are removably insertable in housings 14. Coil housings 14 are location-adjustable on strap 12 so as to be placed to create two perpendicular electromagnetic fields. Strap 12 is also provided with electronic pack 18, which extends from one housing 14, and contains battery 20 and electronic circuitry (see FIGS. 4–6). Strap 12 may be provided as a plastic strap or may be formed from any other flexible material, and is designed with a non-slip surface 21 which contacts the body or cast. Strap 12 functions to hold coil housings 14 in place over the patient's limb at the fracture site, and strap 12 has embedded therein the wires connecting each coil 16 to electronic pack 18.

In a preferred embodiment, housing 14 is constructed to hold coils 16 having approximate dimensions of 30 mm diameter, and 12 mm height. The electronic pack 18 can be constructed with approximate outside dimensions of 35 mm width, 55 mm length, and 22 mm height. These are sample, non-limiting, design dimensions.

In accordance with the principles of the present invention, the use of the term "therapeutic pre-form wrap" is to be understood as one embodiment of a pre-form device for therapeutic purposes, having a shape as a belt, strap 12, bracelet, garment or other suitable matrix, which can provide an immobilization function, since the pre-form wrap can either become a cast, brace or splint, or be integrated into a part of, embedded into, or combined within or under a cast or brace or can be used as a separate device without the immobilization function. The main feature of such a wrap is that it comprises a multi-functional therapeutic cast/bracing device, which integrates an electrotherapeutic system and an immobilization feature. The coils 16 are arranged for seating in a pocket or other portion of the wrap.

Figure 2:
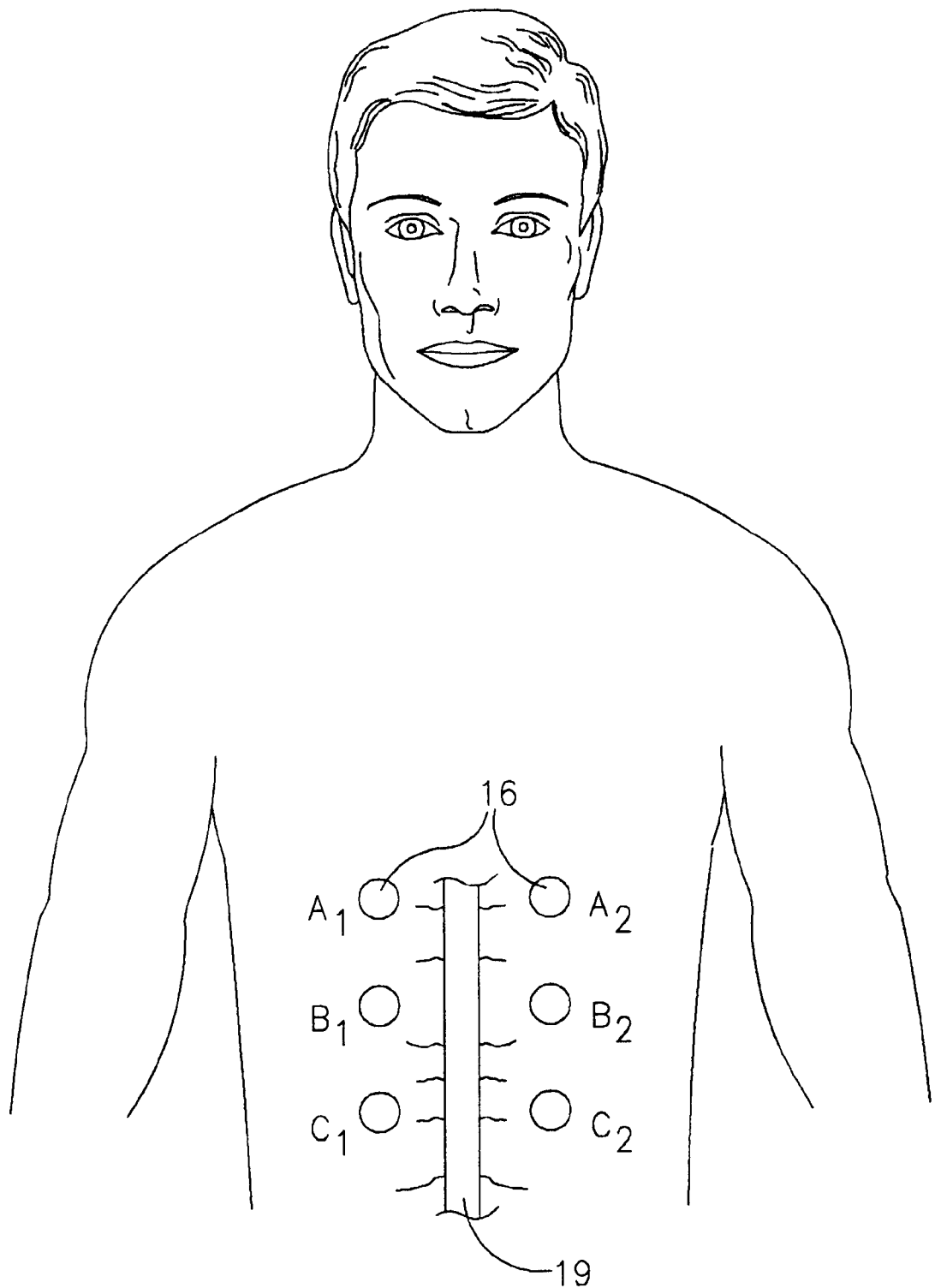
FIG. 2 is an alternative embodiment in which the device of the present invention is used for spinal cord treatment.

As shown in FIG. 2, in use of device 10 for spinal cord treatment, one coil from each pair of coils 16 (A1-A1, B1-B2, C1-C2) is placed on either side of the spinal cord 19, and held in place by a suitably adapted strap or belt like that shown in FIG. 1. In a case of an extended treatment area, additional pairs of coils 16 can be added above the two original pairs and the activation sequence is longitudinal. The connection of these additional coils 16 works in parallel to the original two pairs of coils 16.

Figure 3B:
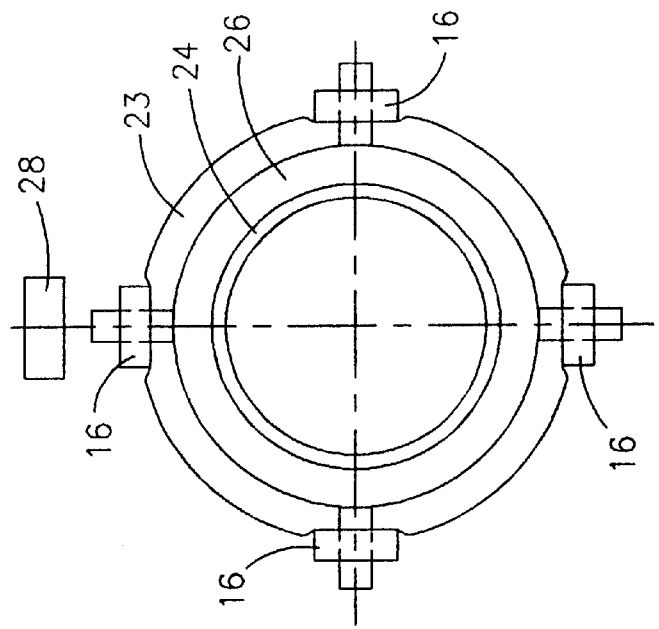
Figure 3A:
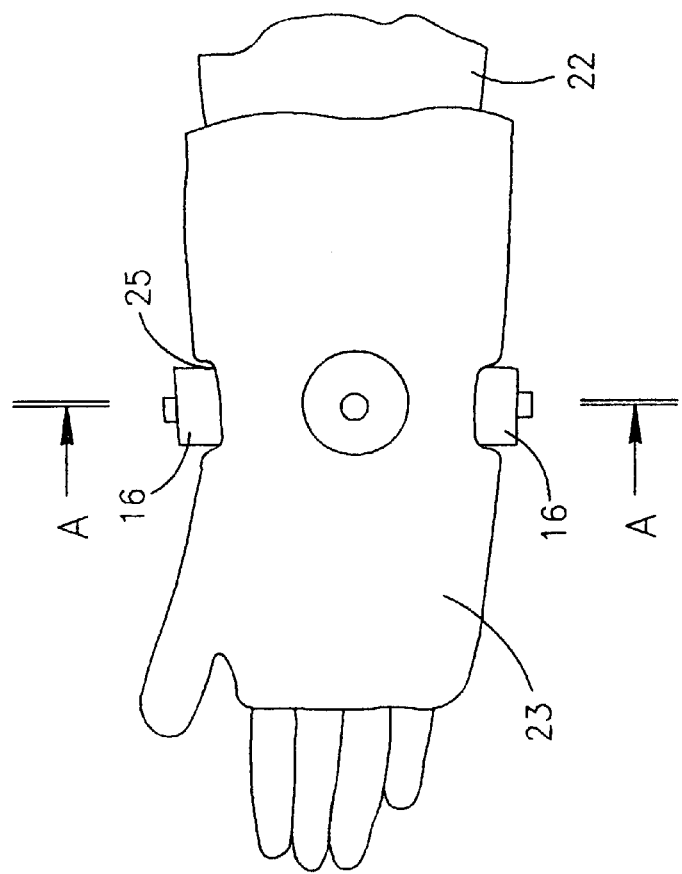
FIG. 3a shows an illustration of the device of the present invention in which the electromagnetic coils are used with a cast placed over a fracture site.

In FIG. 3a, there is shown an illustration of the present invention in which electromagnetic coils 16 are placed over a plaster cast 23 which itself is placed over a limb, e.g. an arm 22. As shown in FIG. 3b, a cross-sectional view taken along section line A—A of FIG. 3a, the area to be immobilized is placed within cast 23 in conventional fashion by first placing a knitted stocking or gauze 24 over arm 22. A layer of cotton lint padding 26 is placed over stocking 24. Coils 16 are placed within pockets 25 formed in cast 23, and strap 12 (not shown in FIG. 3a) holds coils 16 in place around the fracture site. The pockets 25 may be carefully drilled in cast 23 while it is worn over the limb. Electromagnetic coils 16 are provided with connectors 28 on the exterior side which removably connect coils 16 with housing 14 in strap 12. It is to be noted, that once cast 23 is removed, electromagnetic coils 16 may be used by inserting them in device 10, as per FIG. 1, enabling further treatment without using cast 23.

It will be appreciated that the present invention includes embodiments wherein the placement of coils 16 is adapted to be embedded within the cast 23, to increase proximity to the target treatment area, or placed under cast 23.

It will also be appreciated that the embodiment shown relating to an osteogenesis device, can be applied to other biophysical applications, with the necessary changes and adaptations. For example, the placement of the device 10 on the body may be different, and the arrangement of the coils 16 altered, to focus on different parts of the body, for different therapeutic purposes.

Figure 4:
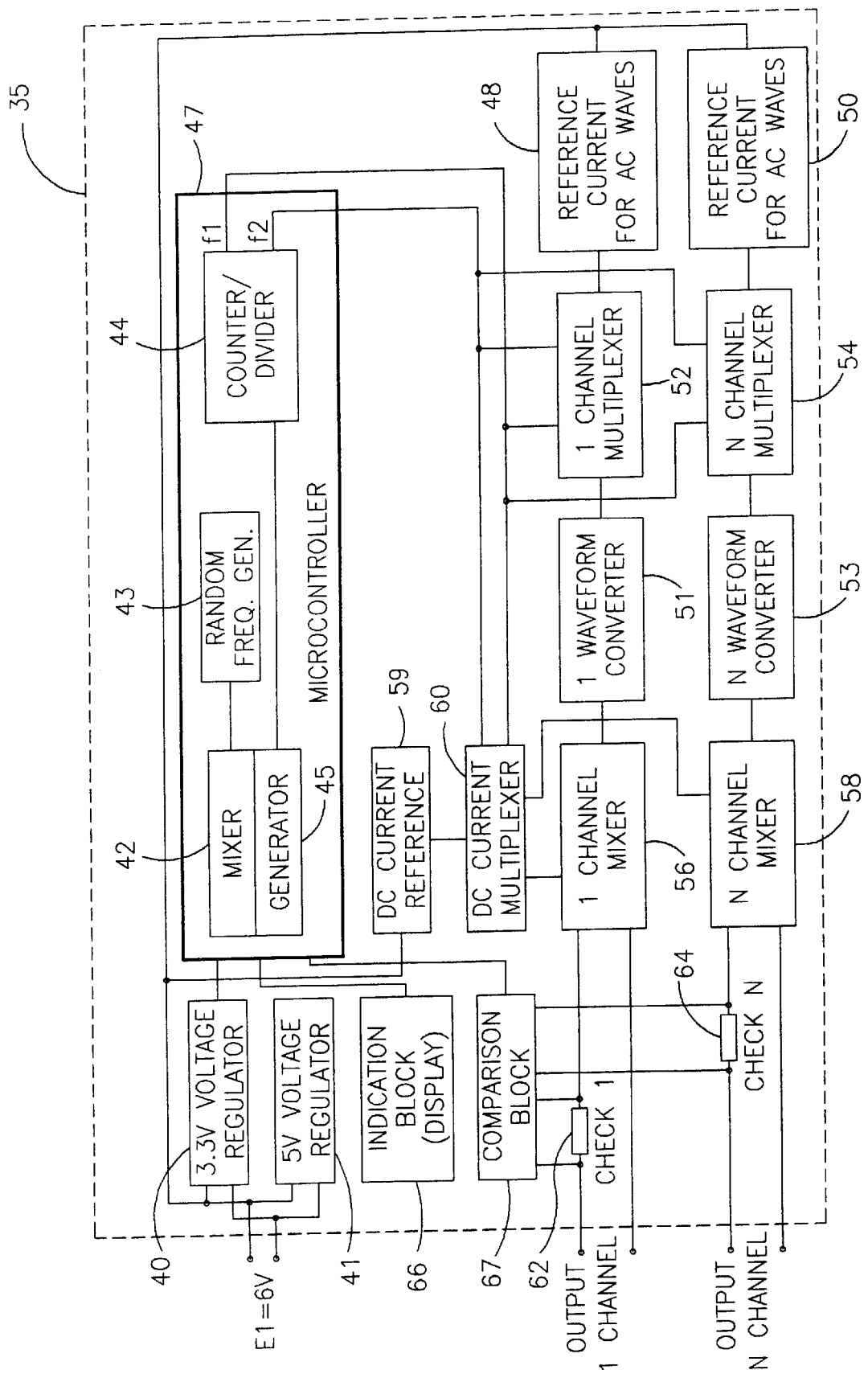
FIG. 4 is an electronic circuit block diagram of the inventive device.

In FIG. 4, there is shown a block diagram of a controller 35 comprising the electronic circuitry used in constructing the PEMF biophysical stimulation field generator device 10. Controller 35 generates the activation signal, which comprises a pulsed high frequency homogeneous field with combined AC/DC electromagnetic fields. The operation of controller 35 is based on microcontroller 47, which executes all device functions. The major function blocks of microcontroller 47 are shown.

In block 40, a voltage regulator is provided for converting the 6.0v input to a stable supply voltage for microcontroller 47, with the goal of decreasing power consumption. A random frequency generator 43 feeds a mixer 42 provided in frequency generator 45, to mix a random frequency with its output. In block 44, a counter/divider executes the function of precise frequency dividing to produce the two required frequencies, 10 KHz and 20 kHz. Reference current blocks 48, 50, 60 produce a stable, constant current, independent of the supply voltage.

Figure 5A:
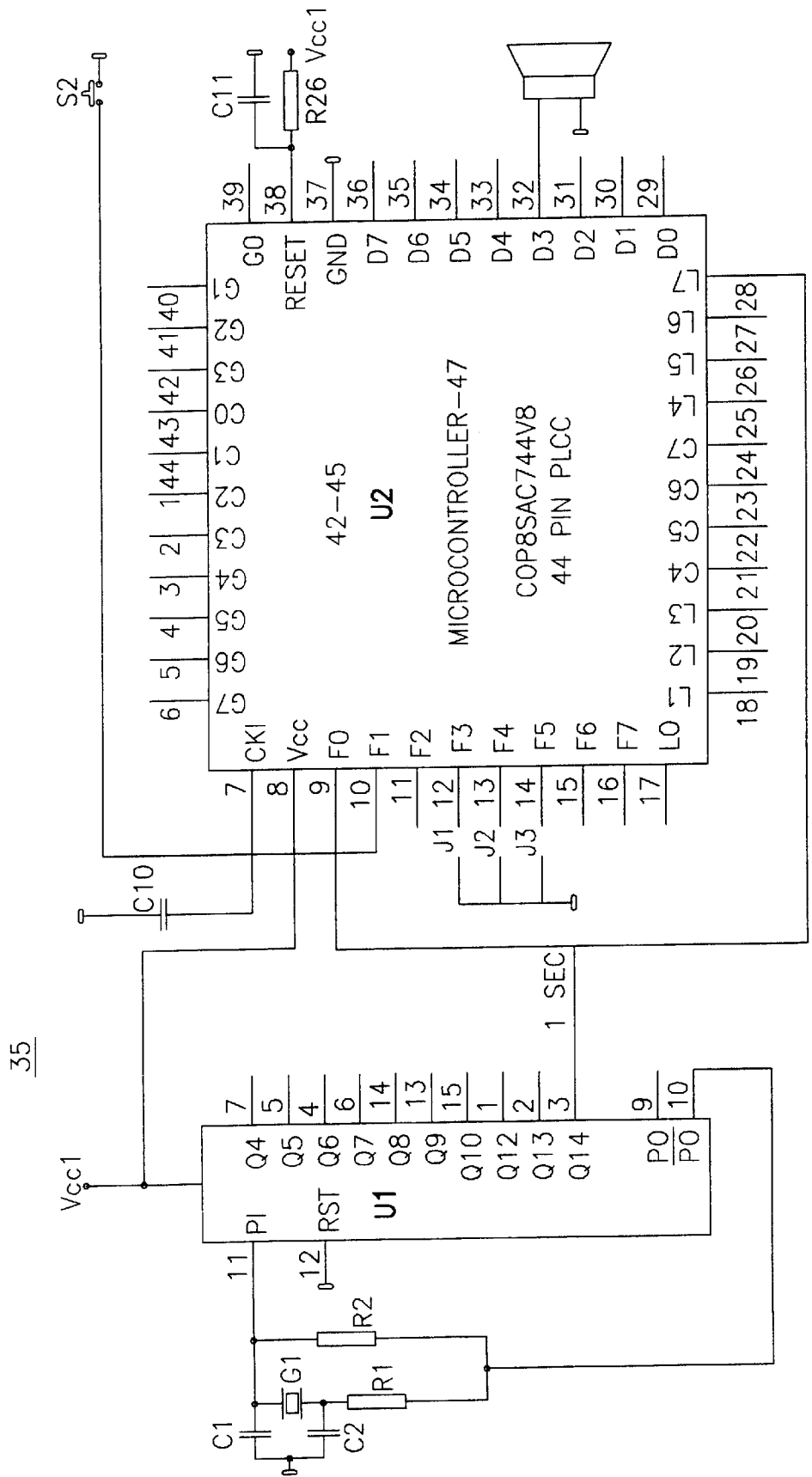
FIGS. 5a–b are detailed electronic schematic diagrams of the inventive device.
Figure 5B:
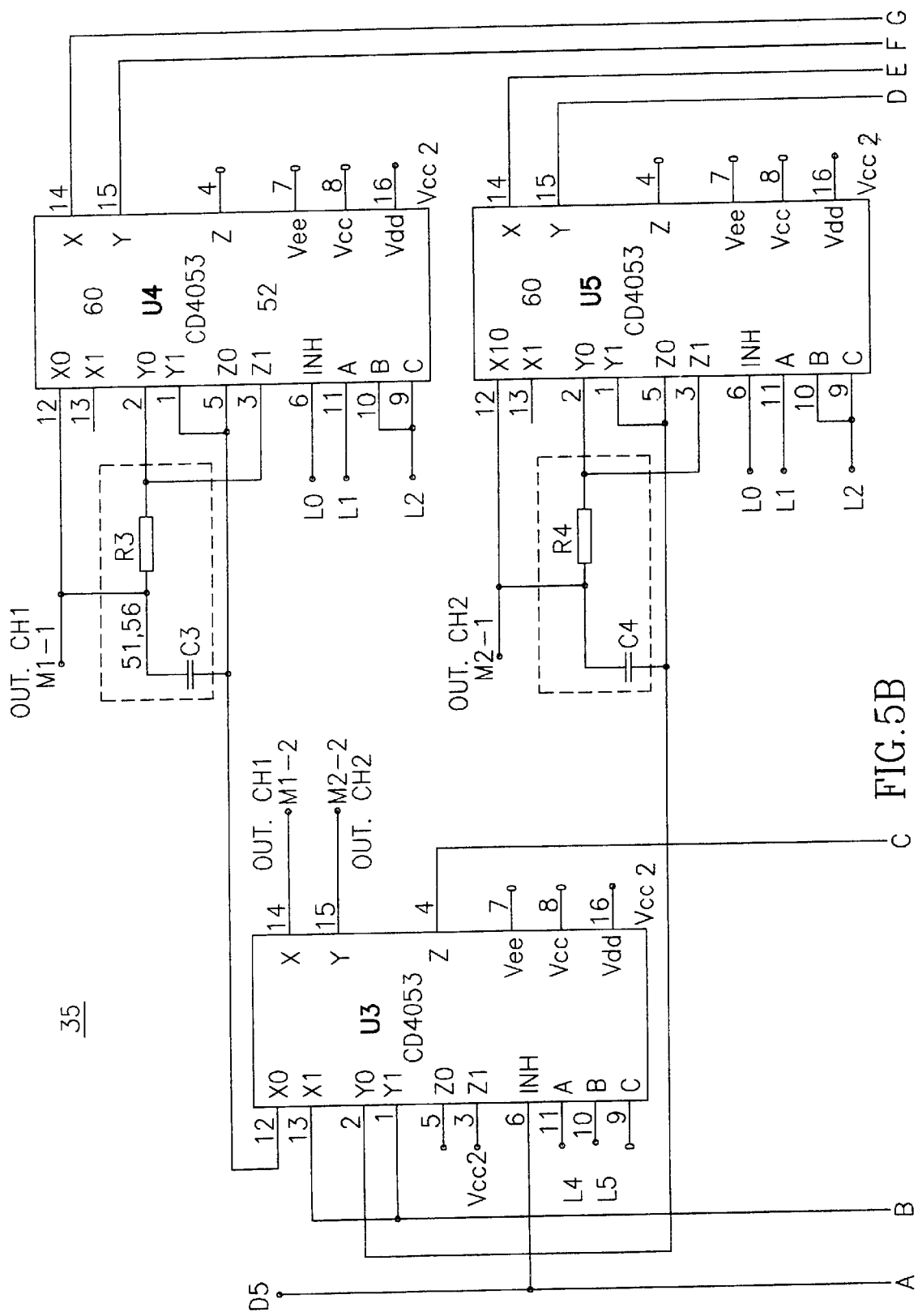
Figure 5C:
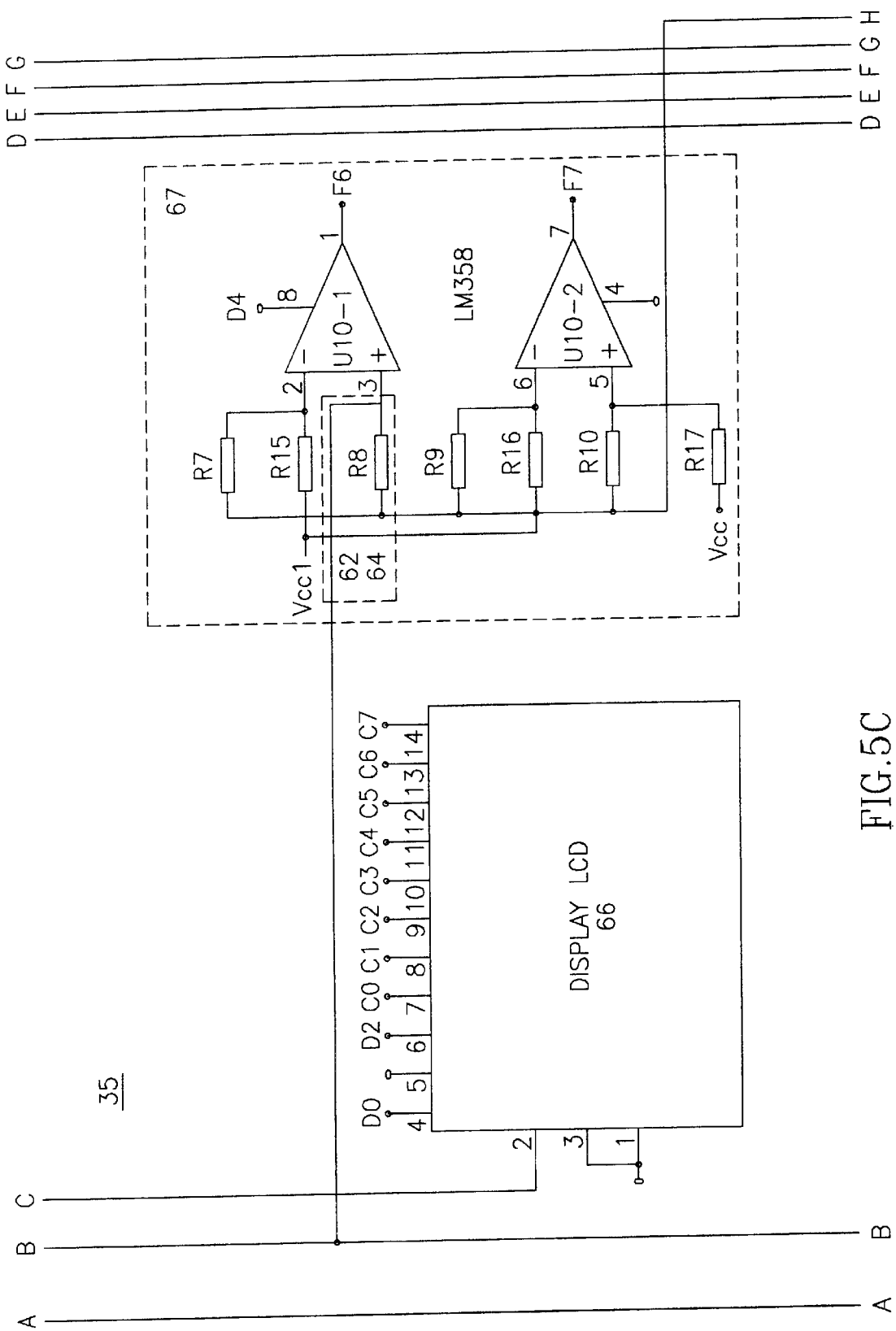
Figure 5D:
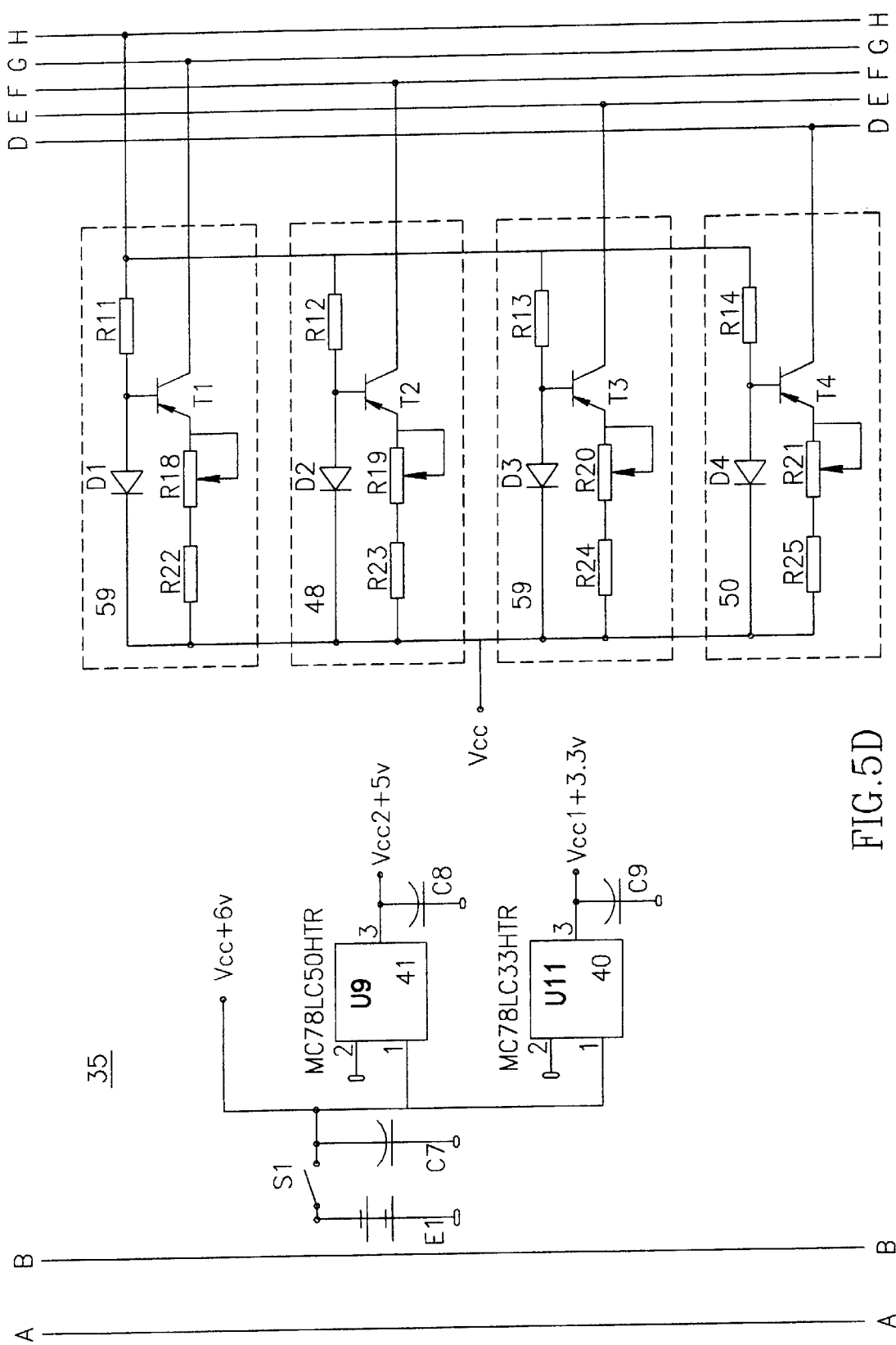
Figure 5E:
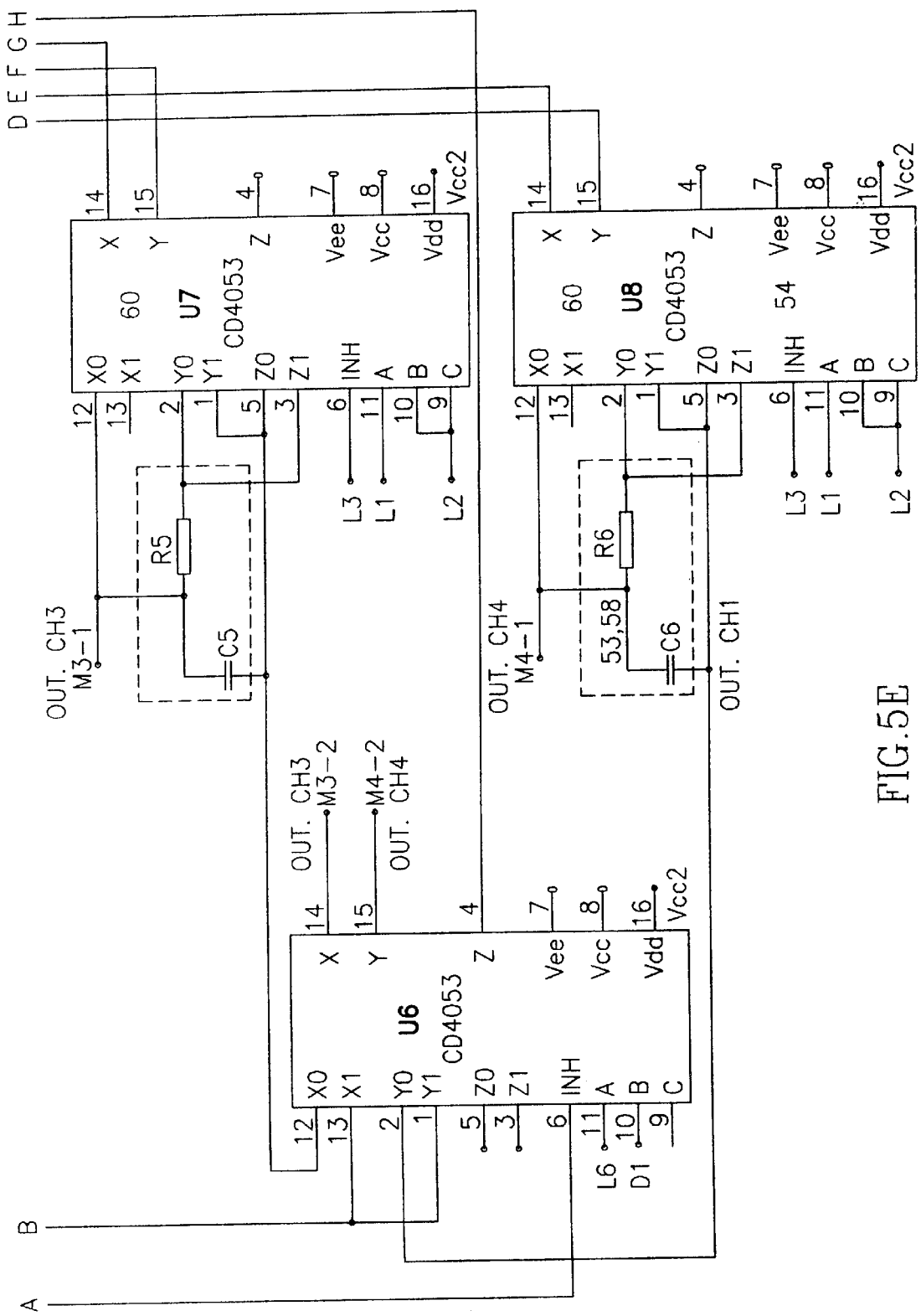

Pulses from the two channel multiplexers 1 and N (blocks 52 and 54, respectively) are fed to the respective wave shape converters (blocks 51 and 52, respectively) which produce two-phased high frequency pulses of 10 kHz (sinusoidal) on low frequency treatment waves (as seen in FIGS. 5a–b). The channel mixers 1 and N (blocks 56 and 58, respectively) mix AC and DC signals, respectively, provided by the corresponding channel multiplexer (for high frequency AC signals) and the constant current reference block 59 and constant current multiplexer block 60 (for DC signals). The output signals are provided on channel 1 and channel N as activation signals, and are fed to electromagnetic coils 16, as shown in FIG. 3, which are sequentially activated. Load resistors check 1 and check N (62 and 64, respectively) test the current fed to coils 16. The results of these tests are compared in comparison block 67 and indicated in indication block 66, which is fed by voltage regulator 41.

In the typical design of devices having medical applications, built-in safety sensors are provided to alert the patient and the medical practitioner of any malfunction.

These safety sensors operate to immediately shut down the device. While not shown in the drawing, these sensors appear in the design, with the alert being provided visually, through LED's or in a printout or display, or acoustically, through an alarm or buzzer. A printout can optionally be provided as a documentation of the procedure, so as to explain fully the course and duration of the treatment.

FIGS. 5a–b are detailed electronic schematic diagrams of controller 35 and FIG. 6 shows a list of component parts typically used in its implementation. The electronic schematic diagram of FIGS. 5a–b and component parts list of FIG. 6 provide additional detail for construction of the electronic circuitry in accordance with skill of the art electronic design techniques. The electronic circuits may be implemented using a microprocessor based on MOSFET design technology (e.g., National Semiconductor COP 8 SAC 744 type), to keep the power consumption of the device 10 very low.

Figure 7:
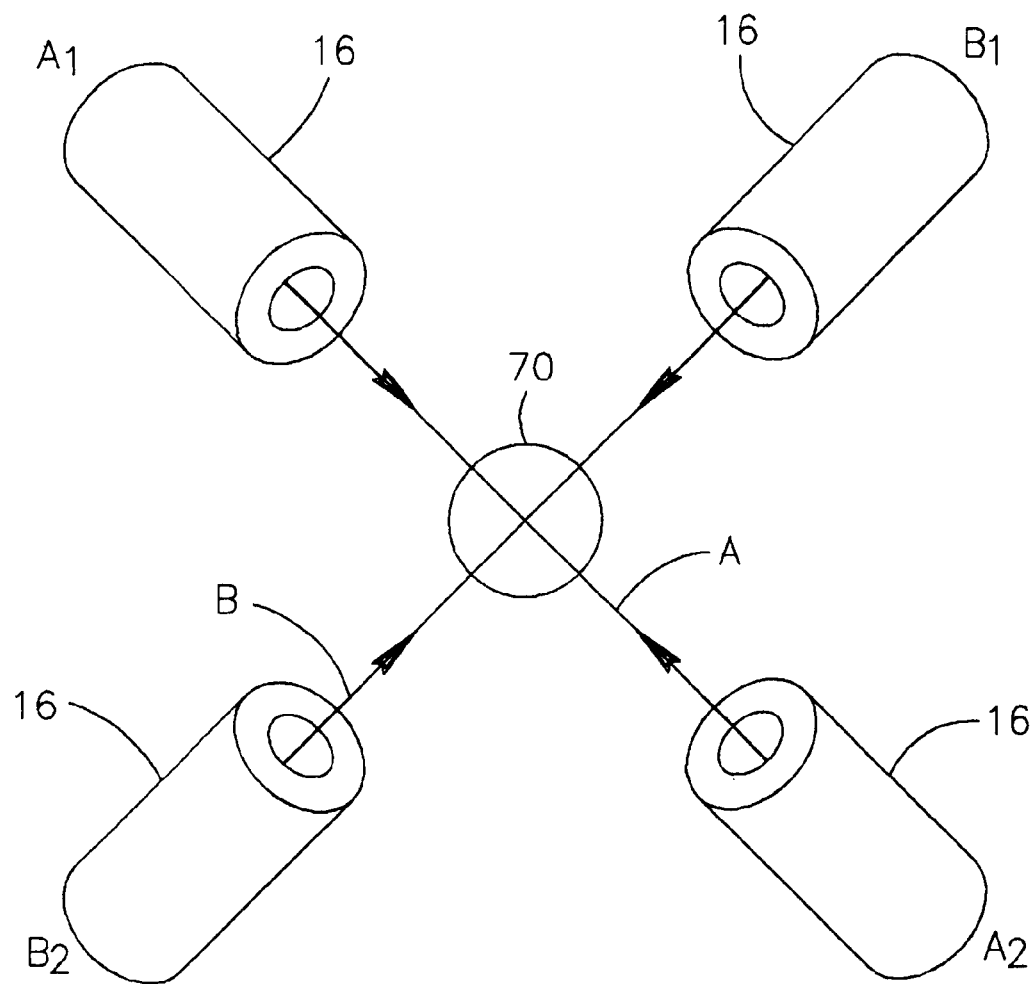
FIG. 7 is a diagrammatic representation of the sequential activation of the electromagnetic coils of FIGS. 1–2, in accordance with an activation signal.

Referring now to FIG. 7, there is shown a diagrammatic representation of the sequential activation of electromagnetic coils 16, in accordance with an activation signal produced by controller 35. Electromagnetic coils 16 are provided in pairs, here marked A1-A2 placed along axis A, and B1-B2 placed along axis B. The pairs operate sequentially providing a homogeneous field around the axis, utilizing an effective transverse execution. The opposing vectorial electromagnetic fields of each pair cause an additive effect of increased magnetic flux at the center of the intersection of the two axes. The sequential operation of the two pairs of magnets provides orthogonal targeting in multiple planes of the treatment site, allowing for a high concentration of field strength at the target area 70. If both axes were to be operated simultaneously, dispersion would occur, reducing the effectiveness. The circular motion of the magnetic field ensures its optimal concentration at the treatment site and decreased energy concentration outside of the treatment site. Since dispersion is limited, no unwanted irradiation of the adjacent tissues occurs.

In accordance with the present invention, controller 35 (FIG. 4) generates a mixed waveform. The mixed waveform represents a species of a PEMF-type waveform, where the species defines the set of optimal parameters for use in treatment of fractures, based on the field strength, frequency etc., all designed to have a physical therapeutic effect to stimulate bone growth.

The main components of this waveform in accordance with the invention, are based on high frequency pulses and symmetric low frequency pulses where the random frequency generator 43, which changes the appearance of the high frequency and low frequency in a random fashion, modulates both. The magnetic flux created by the sequential circular motion, combined with the smaller diameter coils with a ferrite core, provides the optimal concentration of the electromagnetic beam on the treatment area. The random frequency generator 43 provides random modulation to ensure the physiologically needed operation to maintain the long-term effectiveness of the penetrated signals.

The high frequency pulses provide several advantages, including better penetration of the magnetic field via the dielectric tissue, a more homogeneous field which avoids dispersion, with an emphasized directional effect, and better energy utilization of the small cores of the electromagnetic coils 16.

Tissue that is stimulated either rhythmically or from a single direction can learn to accommodate the stimulus and will no longer react. The low frequency pulses are the treatment pulses, and have characteristics that avoid uncontrollable DC polarization, which is inefficient, causing a cancellation effect of the controllable polarization, and reducing to a minimum the electrically excited tissue accommodation, otherwise known as habituation or adaptation. Additionally, the low frequency treatment pulses are designed to eliminate the residual magnetism and thereby achieve optimal benefit with minimum energy investment. In this way, the field that has been designed with symmetrical pulse forms delivered from different angles overcomes the obstacles provided by the physiological mechanisms of the body.

As described previously with regard to FIGS. 4–6, the output of controller 35 appears as a near sinusoidal waveform after passing a wave shape converter included within channel multiplexers 52 and 54.

The inventive device 10 uses a composite technique to promote the efficacy of the treatment and reduce the magnetic radiation to the adjacent tissue. The factors, which contribute to the bone healing properties and minimize harmful side effects, are as follows:

1. Use of small individual electromagnets, provided as coils 16, less than 20 mm in diameter, configured in two pairs, located at 180 degrees from each other.
2. Each pair of coils 16 receives electrical energy from the controller 35, while the time duration of the energizing phases is adjustable.
3. Each pair of coils 16 is energized in a sequential fashion, while the timing of the sequence is adjustable via controller 35.
4. In using device 10 for long bone treatment (i.e., leg and hand), the sequential activation of coils 16 produces a circular motion, thereby attaining maximal field density in the center of the target area where the electromagnetic field is focused (the treatment site).
5. In using the unit for spinal cord treatment, each pair of coils 16 is located on both sides of the spinal cord, and the activation sequence is longitudinal.
6. To achieve a homogeneous magnetic field in the center of the magnetizing coil 16, the magnetic core is made of ferrite material.

The sequential activation of coil pairs 16 occurs within an adjusted time interval, which in the preferred embodiment, is 20 milliseconds. The vectorial magnetic field of each pair is opposing, therefore an additive effect (increased magnetic flux) is created in the center of the axis. Longer time intervals, such as those used by Cakirgil allow this increased magnetic flux to dissipate.

The circular motion of the electromagnetic field ensures its optimal concentration at the treatment site and decreased energy concentration outside of the treatment site. In a case of extended fracture, two additional pairs of coils can be added above the two original pairs. Therefore, the schematic representation is applicable to more than two pairs of magnets, according to the nature of the fracture. The additional coil pairs are connected in parallel to the original two coil pairs 16.

The addition of electromagnetic coils in proximity to the target area, such as by placement along the shaft of the fractured bone, exponentially increases the magnetic flux developed and thereby accelerates healing and reduces the time required.

FIGS. 8a–e show the activation signal waveform diagrams comprising, respectively, a treatment pulse, carrier pulse, mixed waveform, sinusoidal output waveform, and magnetizing current pattern. In FIG. 8a, there is shown a treatment frequency of 50 pulses/sec, with each pulse having a duration of 0.020 sec and a square waveform. FIG. 8b shows the carrier frequency at 10,000 pulses/sec. The carrier wave lowers the body's impedance and allows penetration when the treatment wave is activated. FIG. 8c shows the resultant waveform from the amplitude modulation of the carrier wave with the treatment wave. In FIG. 8d, the generated square pulses are converted to a sinusoidal waveform that is suitable to energizing the magnets. FIG. 8e shows the current pattern via the magnets in which the pulses are 20 millisec on, 20 millisec off.

Figure 9A:
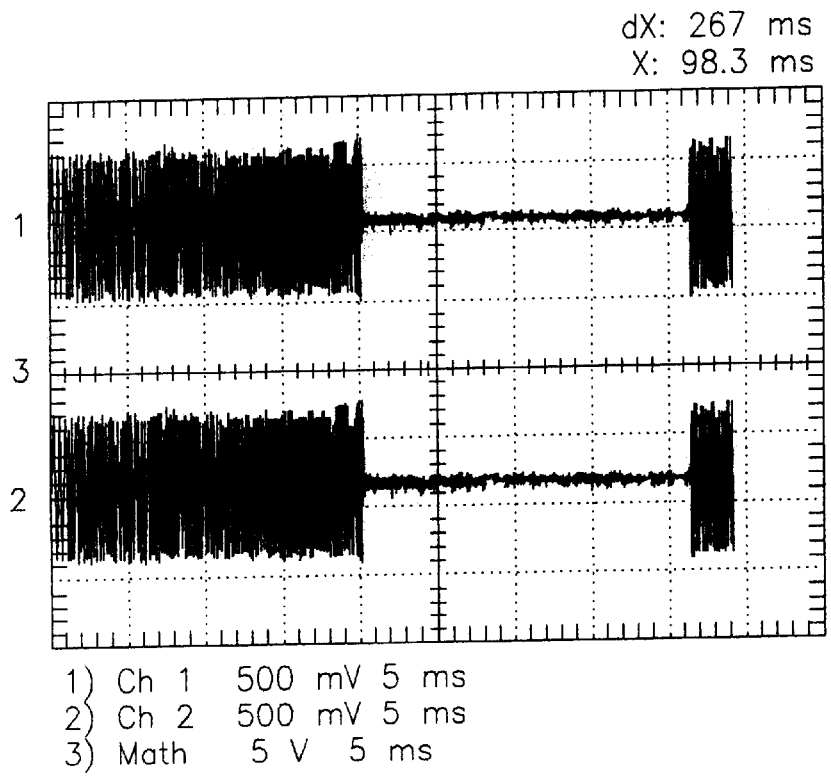
FIGS. 9a–b are oscilloscope waveform patterns, respectively, of the treatment frequency and the carrier frequency.
Figure 9B:
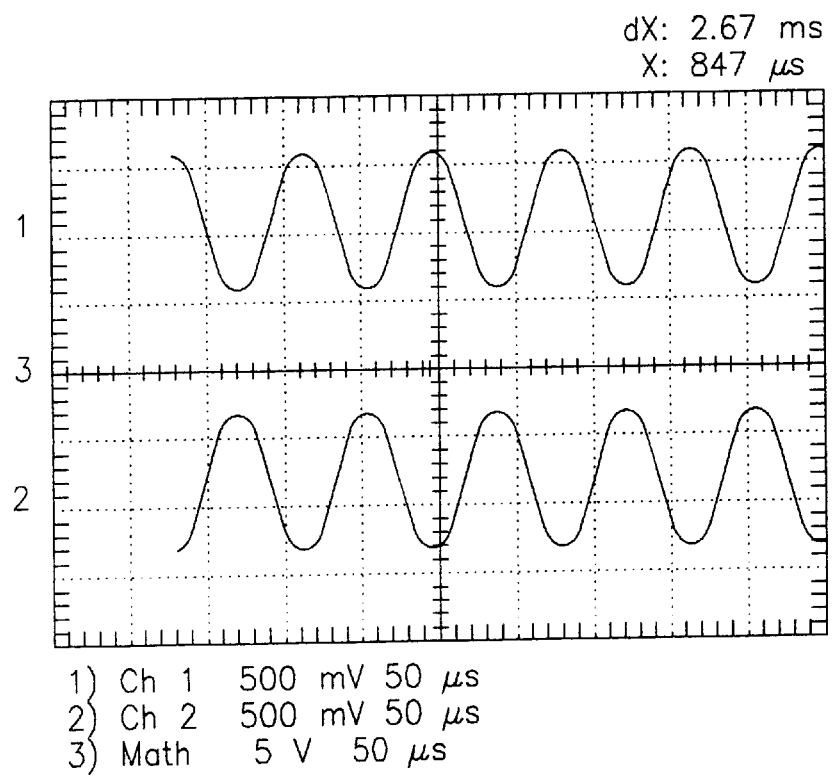

FIGS. 9a–b are oscilloscope waveform patterns, respectively, of the treatment frequency and the carrier frequency, which are developed by the electronic circuitry (see FIGS. 4–6), and are given by way of example. In FIG. 9a, the ON state duration is 20 milliseconds and the OFF state duration is 20 milliseconds. The frequency is 25 Hz and the amplitude is 4V. FIG. 9b illustrates the carrier frequency data in which the frequency is 10 KHz (sinusoidal) and the amplitude is 4V. The output energy develops a magnetic field strength of 2.3 Gauss at the peak and 1.15 Gauss average.

Clinical Studies

Preliminary data using the biophysical stimulation field generator device 10 of the present invention, in an osteogenesis application, is based upon experiments employing pulsed electromagnetic field (PEMF) treatment that have been conducted on three young female dogs. In all three dogs, bone gaps were made using an open procedure in the tibia, whereby on leg (right) served as the "test limb" and the contra-lateral served as the control limb.

The Surgical Procedure

The surgery was carried out under general anesthesia and sterile conditions. All procedures were carried out at the Department of Musculoskeletal Histology at the Technion, Haifa, Isreal, and performed in conformance with the rules and regulations of the National Committee for Ethics in Animal Experimentation. Each animal was housed in an individual cage and checked daily for any signs of morbidity, including difficulty in mobility behavioral changes, appetite and body temperature.

The Surgical Procedure Protocol

The surgery involved the creation of a bone gap in the mid-portion of the tibia, measuring 1.0×1.5 cm. This gap included the outer cortical portion of the tibia, thus leaving the bone marrow of the operative site exposed to the underlying tissues of the skin. The wound was closed in layers and the animal received 1 gram of penicillin per day for three days.

The same exact procedure was performed on both hind legs. The osteotomies were carried out using an air driven Striker Bone Saw while the bone was cooled with sterile saline. The animals were allowed to recover for 3–4 days before initiating PEMF treatment.

Experimental Set-up

Experiments were conducted taking into consideration the following parameters:
a. Time/schedule of treatment:
  Weekly schedule—Sun., Mon., Tues., Wed., Thurs., Fri.: daily treatment cycle of one hour of treatment, a two-hour break and one additional hour of treatment. During the break between treatments, the dogs were returned to their same cages.
b. Equipment—animal immobilization sling, osteogenesis device 10 of the present invention and an FW Bell Model 5080 Magnetometer/Gaussmeter.
c. PEMF treatment protocol was carried out by having the experimental animal immobilized in a sling. The osteogenesis device and electrodes were checked and measured for the specified and required "PEMF species" output by a magnetometer prior to each treatment session. The electromagnetic electrodes thereafter were placed directly perpendicular to and over the exact target treatment sites area. The electromagnet was embedded in a functionally immobilizing 3M® Softcast™, not in direct contact, but very close proximally to the skin. The Softcast™ containing the embedded electromagnetic electrode was taken off the subject's leg after each experimental session.
d. The behavior and response of animals were recorded at each session, while the animals were not under the influence of drugs.
e. The tolerance of the animals allowed us to repeat the treatment for six consecutive weeks. The animals were conditioned to the treatment program by the end of the first week.
f. There were no problems regarding the animals' mobility, appetite, behavior, etc.
g. Blood samples for general hematological parameters included:
  1. Red Blood Cells
  2. Hemoglobin
  3. Hematocrit
  4. White Blood Cells:
    a. White Blood Cell Differential
      a1. Polymorphonuclear Cells
      a2. STABS
      a3. Lymphocytes
      a4. Monocytes
      a5. Eosinophils
      a6. Basophils
  5. Platelets
  6. Blood Chemistry
    a. Albumin Total Protein
    b. Creatinine
    c. Blood Urinary Nitrogen
    d. Glucose
    e. Alkaline Phosphatase
    f. SGPT
    g. Calcium Phosphatase Following the experimental period, the animals were subjected to Computerized Tomography (CT) tests. For this purpose, the most updated CT equipment was applied to this experimental population of dogs.

The results are of high quality, demonstrating the gradation of the bone wound healing, callus formation, mineralization, bone remodeling, de-novo development of cortical bone in the injured sites (experimental and control) and their environment.

The animals were sacrificed under general anesthesia and the mid-portions of both tibia were excised and immediately transferred into a fixative consisting of para-formaldehyde 2.5% (pH 7.2). The fixation period lasted two weeks (14 days), at room temperature, during which the fixative solution was changed every four days. The fixative/specimen ratio was 70:1. Following fixation, specimens were transferred into a 10% formic acid solution for decalcification. All specimens were immersed in a large amount of decalcifier and stirred by a magnetic stirrer at room temperature. Specimens were checked manually every five days to determine their suitability for embedding in either paraffin or JB4 Resin.

Following decalcification, all specimens were washed for over 24 hours in distilled water at room temperature and afterwards underwent dehydration in a series of alcohol concentrations, cleared in xylene and embedded in either paraffin or resin. Embedded tissues were cut to 6 micron thickness with a JUNG RM265 Microtome and stained with either 1% Touledine Blue or Hematoxylin and Eosin. Stained sections were examined under a Zeiss-Axyophot microscope. Four microphotograph Ektochrome 160 films were used for color slides and professional AgfaPan 25 film was used for black and white prints.

During sacrifice, biopsies were obtained from major internal organs such as lungs, liver, spleen, kidneys and lymph nodes.

Preliminary Findings

The wounds in all animals healed unremarkably. In one case a transient local swelling was noted, which subsided after one week. The CT scans taken after 6 weeks of treatment revealed an appreciably advanced stage of healing and tissue regeneration in legs that had received PEMF Therapy, whereas in the control specimens a large, unorganized callus was apparent. The stage of bone regeneration was much more advanced in bones that had been exposed to PEMF intervention and did not differ from that of intact tibiae.

Histologically, one could identify a significant difference between test and control specimens. New bone formation appeared to occupy larger areas within the injured gaps in treated bones. The new bone appeared healthy, and consisted mainly of new bone trabeculae. The latter demonstrated many newly formed lacunae that were occupied with new osteocytes. A well developed periosteum was noted, along with multi-nucleated osteoclasts along the external periphery of the healing bone. Bone marrow tissue was also noted between the new bone trabeculae and new blood vessels. A unique feature noted in PEMF treated specimens related to the development of a "bone envelope" around the original tibia, which could serve as an additional mechanical support to the injured bone. This finding could possibly indicate that periosteal cells on the opposite side of the gap responded to the PEMF therapy and created de-novo formation of osseous tissue.

In comparison to the control specimens, the test specimens exhibited a substantial increase in the amount of new bone formation at the treatment, or defect site, of approximately 50%, within 2.5 weeks during the post-operative period.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

What is claimed is:

1. An activation signal used for generating a PEMF biophysical stimulation field for biomedical applications, applied to at least two pairs of electromagnetic coils, individual ones of each pair being arranged on a pre-form wrap at the respective opposite ends of a pair of orthogonal axes, with said pre-form wrap being disposed proximate a target area, said activation signal comprising:

a pulsed energy level having a random frequency component, comprising a relatively high frequency carrier wave amplitude-modulated by a relatively low frequency treatment wave, wherein said amplitude-modulation introduces a random frequency pattern, said pulsed energy level being applied simultaneously to individual ones of said oppositely arranged coil pair so as to produce oppositely-directed pulsed electromagnetic fields, and subsequently to the other of said oppositely-arranged coil pair, in sequential, alternating fashion.

2. The signal of claim 1 wherein said pulsed energy level comprises a mixed waveform combined frequency signal, having a high frequency component defining said carrier wave substantially within a range of 10,000 pulses/sec, and a low frequency component defining a square waveform treatment frequency of 25 pulses/sec, each having a duration of 0.020 sec.

3. The signal of claim 2 wherein said square wave treatment frequency avoids uncontrollable DC polarization of said at least one electromagnetic coil, and reduces electrically excited tissue accommodation to a minimum level.

4. The signal of claim 1 wherein said electromagnetic coils develop a current pattern, having a duty cycle of between 5–30 msec ON, and between 5–30 msec OFF.

5. The signal of claim 1 wherein said electromagnetic coils develop a current pattern in said electromagnetic coils, having a duty cycle of 20 msec ON, and 20 msec OFF.

6. The signal of claim 1 wherein each of said coil pairs develops a magnetic field strength of 2.3 Gauss peak and 1.15 Gauss average.

7. The signal of claim 1 simultaneously applied to individual ones of said oppositely arranged coil pair so as to produce oppositely-directed electromagnetic fields, and subsequently applied simultaneously to the other of said oppositely-arranged coil pair, in sequential, alternating fashion, to develop a rotating magnetic field focussed at a treatment site.

8. The signal of claim 7 wherein said focussed, sequentially rotating magnetic field ensures optimal concentration of magnetic flux at said treatment site and decreased energy concentration outside of said treatment site, limiting unwanted dispersion and irradiation of adjacent tissues.

9. The signal of claim 1 wherein each of said oppositely arranged coil pair develops an opposing sequentially alternating vectoral pulsed magnetic field along the axis defined between them, causing said pair of opposing sequentially alternating vectoral magnetic fields to enhance having an additive effect of increased magnetic flux at the center of the intersection of said coil pair axes.

10. A PEMF osteogenesis stimulation device comprising:

a pre-form wrap for placement in proximity to a body portion intended for therapy;

at least two pairs of electromagnetic coils, individual ones of each pair being arranged on said pre-form wrap at the respective opposite ends of a pair of orthogonal axes;

means for generating a pulsed activation signal applied simultaneously to individual ones of said oppositely arranged coil pair so as to produce oppositely-directed pulsed electromagnetic fields, and subsequently to the other of said oppositely-arranged coil pair, in sequential, alternating fashion, said activation signal having a random frequency component, wherein said activation signal provides PEMF stimulation comprising a relatively high frequency carrier wave amplitude-modulated by a relatively low frequency treatment wave, and wherein said amplitude-modulation introduces a random frequency pattern.

11. The device of claim 10 wherein said pre-form wrap comprises a strap having a plurality of coil housings formed therein about its circumference, each of said at least two pairs of electromagnetic coils being disposed within one of said coil housings, said strap being adapted for placement over a bone fracture treatment site.

12. The device of claim 11 wherein said strap is adapted to be placed over a cast.

13. The device of claim 11 wherein said electromagnetic coils are removably insertable within said coil housings, and are operable separately from them.

14. The device of claim 10 wherein said pre-form wrap has formed therein pockets for embedding said electromagnetic coils therein, said pre-form wrap being adapted for placement over a bone fracture treatment site.

15. The device of claim 10 wherein said pre-form wrap is adapted to be placed under a cast.

16. The device of claim 10 wherein said generating means comprises electronic circuitry for providing said activation signal as a mixed waveform combined frequency signal, having a high frequency component defining said carrier wave substantially within a range of 10,000 pulses/sec, and a low frequency component defining a square waveform treatment frequency of 25 pulses/sec, each having a duration of 0.020 sec.

17. The device of claim 16 wherein said square wave treatment frequency avoids uncontrollable DC polarization of said electromagnetic coils, and reduces electrically excited tissue accommodation to a minimum level.

18. The device of claim 10 wherein said activation signal develops a current pattern in said electromagnetic coils, having a duty cycle of between 5–30 msec ON, and between 5–30 msec OFF.

19. The device of claim 10 wherein said activation signal develops a current pattern in said electromagnetic coils, having a duty cycle of 20 msec ON, and 20 msec OFF.

20. The device of claim 10 wherein said activation signal develops a magnetic field(s) strength in each of said coil pairs of 2.3 Gauss peak and 1.15 Gauss average.

21. The device of claim 10 wherein said pulsed activation signal is simultaneously applied to individual ones of said oppositely arranged coil pair so as to produce oppositely-directed electromagnetic fields, and subsequently applied simultaneously to the other of said oppositely-arranged coil pair, in sequential, alternating fashion, to develop a rotating magnetic field focussed at a treatment site.

22. The device of claim 20 wherein said focussed, sequentially rotating magnetic field ensures optimal concentration of magnetic flux at said treatment site and decreased energy concentration outside of said treatment site, limiting unwanted dispersion and irradiation of adjacent tissues.

23. The device of claim 10 wherein each of said oppositely arranged coil pair develops an opposing sequentially alternating vectoral pulsed magnetic field along the axis defined between them, causing said pair of opposing sequentially alternating vectoral magnetic fields to enhance having an additive effect of increased magnetic flux at the center of the intersection of said coil pair axes.

24. The device of claim 10 wherein said PEMF stimulation develops an electrical field in muscle tissue, developing therein tetanic muscle stimulating microcontractions, thereby offsetting muscle atrophy, whereby said microcontractions provide a desired muscular exercise loading on bone, and simultaneously stimulate bone growth.

25. A method of promoting fracture healing and osteogenesis at a treatment site comprising the steps of:
providing a pre-form wrap for placement in proximity to a body portion intended for therapy;
providing at least two pairs of electromagnetic coils, individual ones of each pair being arranged on said pre-form wrap at the respective opposite ends of a pair of orthogonal axes;
generating a pulsed activation signal applied simultaneously to individual ones of said oppositely arranged coil pair so as to produce oppositely-directed pulsed electromagnetic fields, and subsequently to the other of said oppositely-arranged coil pair, in sequential, alternating fashion, said activation signal having a random frequency component,
wherein said activation signal provides PEMF stimulation to the treatment site comprising a relatively high frequency carrier wave amplitude-modulated by a relatively low frequency treatment wave,
and wherein said amplitude-modulation introduces a random frequency pattern.

26. The method of claim 25 wherein said at least two pairs of electromagnetic coils are arranged on said pre-form wrap for placement over a bone fracture treatment site.

27. The method of claim 25 wherein said at least two pairs of electromagnetic coils are arranged on said pre-form wrap for placement over a cast.

28. The method of claim 25 wherein said at least two pairs of electromagnetic coils are arranged on said pre-form wrap for placement under a cast.

29. The method of claim 25 wherein said generating step is performed by means comprising electronic circuitry for providing said activation signal as a mixed waveform combined frequency signal, having a high frequency component defining a carrier wave substantially within a range of 10,000 pulses/sec, and a low frequency component defining a square waveform treatment frequency of 25 pulses/sec, each having a duration of 0.020 sec.

30. The method of claim 29 wherein said low frequency pulses act as treatment pulses, which avoid uncontrollable DC polarization of said electromagnetic coils, and reduce electrically excited tissue accommodation to a minimum level.

31. The method of claim 25 wherein said activation signal develops a current pattern in said electromagnetic coils, having a duty cycle of between 5–30 msec ON, and between 5–30 msec OFF.

32. The method of claim 25 wherein said activation signal develops a current pattern in said electromagnetic coils, having a duty cycle of 20 msec ON, and 20 msec OFF.

33. The method of claim 25 wherein said activation signal develops a magnetic field strength in each of said coil pairs of 2.3 Gauss peak and 1.15 Gauss average.

34. The method of claim 25 wherein said pulsed activation signal is simultaneously applied to individual ones of said oppositely arranged coil pair so as to produce oppositely-directed electromagnetic fields, and subsequently applied simultaneously to the other of said oppositely-arranged coil pair, in alternating, sequential fashion, to develop a rotating magnetic field focussed at a treatment site.

35. The method of claim 34 wherein said focussed sequentially rotating magnetic field ensures optimal concentration of magnetic flux at said treatment site and decreased energy concentration outside of said treatment site, limiting unwanted dispersion and irradiation of adjacent tissues.

36. The method of claim 25 wherein each of said oppositely arranged coil pair develops an opposing vectorial magnetic field along the axis defined between them, causing said pair of opposing vectorial magnetic fields to have an additive effect of increased magnetic flux at the center of the intersection of said coil pair axes.

37. The method of claim 25 wherein said PEMF stimulation develops an electrical field in muscle tissue, developing therein tetanic microcontractions, thereby offsetting muscle atrophy and creating gentle exercise loading, inducing bone growth stimulation.

38. The method of claim 25 for providing a physiological response in the form of observed osteogenesis comprising a substantial increase in new bone formation at the treatment site, within 2.5 weeks of treatment during a post-operative recovery period.

39. An integrated, multi-functional osteogenesis healing system comprising a PEMF osteogenesis stimulation device operable by application of an activation signal for producing a physiological result in the form of at least one of osteogenesis, soft tissue therapy and muscle stimulation, said system comprising:

a pre-form wrap for placement in proximity to a body portion intended for therapy, said body portion being immobilized by said wrap;

at least two pairs of electromagnetic coils, individual ones of each pair being arranged on said pre-form wrap at the respective opposite ends of a pair of orthogonal axes;

means for applying a pulsed activation signal simultaneously to individual ones of said oppositely arranged coil pair so as to produce oppositely-directed pulsed electromagnetic fields, and subsequently to the other of said oppositely-arranged coil pair, in sequential, alternating fashion, said activation signal having a random frequency component, wherein said activation signal provides PEMF stimulation comprising a relatively high frequency carrier wave amplitude-modulated by a relatively low frequency treatment wave, wherein said amplitude-modulation introduces a random frequency pattern, and wherein said pulsed activation signal comprises a mixed waveform combined frequency signal, having a high frequency component defining said carrier wave substantially within a range of 10,000 pulses/sec, and a low frequency component defining a square waveform treatment frequency of 25 pulses/sec, each having a duration of 0.020 sec.

40. A PEMF biophysical stimulation field for biomedical applications, produced by applying an activation signal to at least two pairs of electromagnetic coils, individual ones of each pair being arranged on a pre-form wrap at the respective opposite ends of a pair of orthogonal axes, with said pre-form wrap being disposed proximate a target area, said PEMF biophysical stimulation field comprising:

a pulsed energy level having a random frequency component, comprising a relatively high frequency carrier wave amplitude-modulated by a relatively low frequency treatment wave, wherein said amplitude-modulation introduces a random frequency pattern, said pulsed energy level existing simultaneously in individual ones of said oppositely arranged coil pair so as to produce oppositely-directed pulsed electromagnetic fields, and subsequently existing in the other of said oppositely-arranged coil pair, in sequential, alternating fashion, wherein said activation signal comprises a mixed waveform combined frequency signal, having a high frequency component defining said carrier wave substantially within a range of 10,000 pulses/sec, and a low frequency component defining a square waveform treatment frequency of 25 pulses/sec, each having a duration of 0.020 sec, said activation signal developing a current pattern in said electromagnetic coils, having a duty cycle of between 5–30 msec ON, and between 5–30 msec OFF, and said activation signal developing a magnetic field strength in each of said coil pairs of 2.3 Gauss peak and 1.15 Gauss average.

41. An integrated PEMF biophysical stimulation healing system for use at a treatment site comprising:

a pre-form wrap for placement in proximity to a body portion at the treatment site intended for therapy, said body portion being immobilized by said wrap;

an electrotherapeutic system comprising a plurality of electromagnetic coils and an electromagnetic field generator operable to activate said coils by applying thereto a pre-selected activation signal, said activation signal developing pulsed electromagnetic fields focussed at the treatment site, for providing biophysical stimulation associated with healing.

* * * * *